(12) United States Patent
Greenberg et al.

(10) Patent No.: US 8,019,428 B2
(45) Date of Patent: *Sep. 13, 2011

(54) VIDEO PROCESSING METHODS FOR IMPROVING VISUAL ACUITY AND/OR PERCEIVED IMAGE RESOLUTION

(75) Inventors: Robert J. Greenberg, Los Angeles, CA (US); Richard P. Williamson, Sherman Oaks, CA (US); Joseph H. Schulman, Santa Clarita, CA (US); Reza P. Rassool, Stevenson Ranch, CA (US); Lee J. Mandell, West Hills, CA (US); Abraham N. Seidman, Beverly Hills, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 942 days.

This patent is subject to a terminal disclaimer.

(21) Appl. No.: 11/880,045

(22) Filed: Jul. 19, 2007

(65) Prior Publication Data
US 2007/0299484 A1 Dec. 27, 2007

Related U.S. Application Data

(62) Division of application No. 11/115,620, filed on Apr. 27, 2005, now Pat. No. 7,266,413, which is a division of application No. 09/851,268, filed on May 7, 2001, now Pat. No. 6,920,358.

(60) Provisional application No. 60/207,529, filed on May 26, 2000.

(51) Int. Cl.
*A61N 1/00* (2006.01)

(52) U.S. Cl. .................................................. 607/54

(58) Field of Classification Search .................. None
See application file for complete search history.

(56) References Cited

U.S. PATENT DOCUMENTS
4,628,933 A 12/1986 Michelson
(Continued)

FOREIGN PATENT DOCUMENTS
WO WO 00/56393 8/2000

OTHER PUBLICATIONS

Eckmiller, Rolf; Learning Retina Implants with Epiretinal Contacts; Ophthalmic Research; Ophthalmic Res 1997; 29: pp. 281-289.

(Continued)

*Primary Examiner* — Mark W Bockelman
(74) *Attorney, Agent, or Firm* — Scott B. Dunbar; Tomas Lendvai

(57) ABSTRACT

A method and apparatus for improving visual acuity when providing a visual image from a "high" resolution input device to a "low" resolution output device. The described invention is of particular use when the output device is an array of electrodes as part of a retinal prosthesis used to restore vision to a visually-impaired patient. In that various limitations may, within the foreseeable future, limit the density of such an electrode array (and thus the resolution of the output image), the present invention teaches techniques to assign processed pixel subsets of a higher resolution image to a single electrode. By varying the pixel subsets, e.g., by jittering, and/or altering the processing criteria, the perceived visual acuity may be further improved. Alternatively and additionally, such processing may be further extended to drive neighboring electrodes in combination to thus stimulate virtual electrode sites and thus further enhance visual acuity.

12 Claims, 19 Drawing Sheets

U.S. PATENT DOCUMENTS

| | | | |
|---|---|---|---|
| 5,109,844 A | 5/1992 | de Juan, Jr. | |
| 5,935,155 A | 8/1999 | Humayun et al. | |
| 6,920,358 B2 * | 7/2005 | Greenberg et al. | 607/54 |
| 7,266,413 B2 * | 9/2007 | Greenberg et al. | 607/54 |

OTHER PUBLICATIONS

Brindley, et al., G.S.; The Sensations Produced by Electrical Stimulation of the Visual Cortex; J. Physiol. (1968), 196, pp. 479-493.

* cited by examiner

FIG. 4 | FIG. 5
--- | ---
WITHOUT ENHANCED ACUITY FILTER | WITH ENHANCED ACUITY FILTER
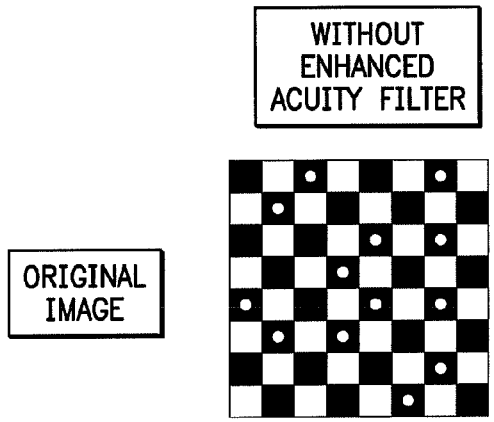
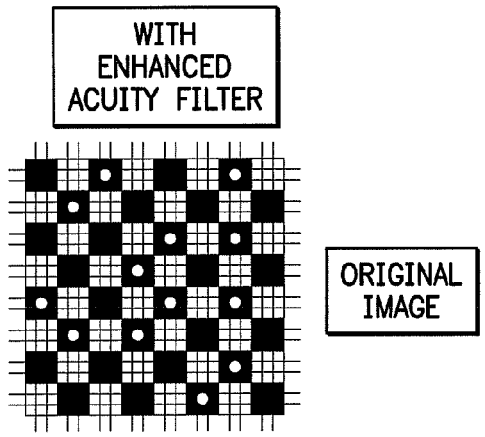
ORIGINAL IMAGE | ORIGINAL IMAGE
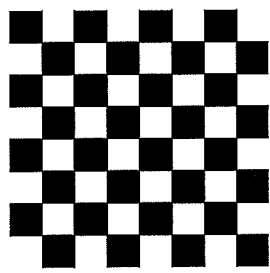
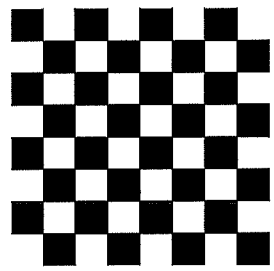
4A) ALIGNED | 5A) ONLY TOP CORNER
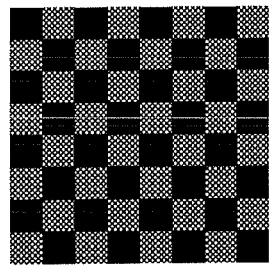
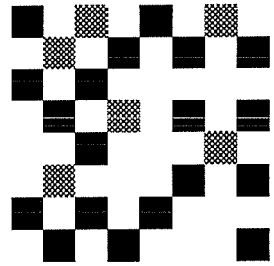
4B) 25% MISALIGNED | 5B) ONLY CENTER
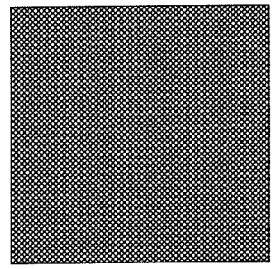
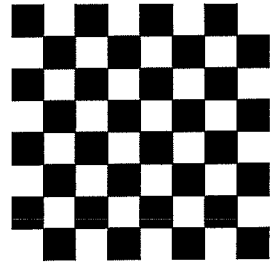
4C) 50% MISALIGNED | 5C) ONLY BOTTOM

|   | T1 | T2 | T3 | T4 | T5 | T6 | T7 | T8 | T9 | T10 | T11 | T12 |
|---|---|---|---|---|---|---|---|---|---|---|---|---|
| A |   | A/B=A' |   | A/E=A'' |   |   |   |   |   |   |   |   |
| B |   | B/C=B' | B/F=B'' |   |   | B/E=B''' |   |   |   |   | B/G=B'''' |   |
| C |   | C/D=C' | C/G=C'' |   |   |   | C/H=C''' |   |   |   |   |   |
| D |   |   | D/H=D'' |   |   |   |   |   |   |   |   |   |
| E |   | E/F=E' |   |   | E/I=E'' |   |   | E/J=E''' |   |   |   |   |
| F |   |   | F/G=F' |   | F/J=F'' |   |   |   | F/K=F''' |   |   |   |
| G |   | G/H=G' |   |   | G/K=G'' |   |   |   |   | G/L=G''' |   |   |
| H |   |   |   |   | H/L=H'' |   |   |   |   |   |   |   |
| I |   | I/J=I' |   | I/M=I'' |   |   | I/N=I''' |   |   |   |   |   |
| J |   |   | J/K=J' | J/N=J'' |   |   |   |   |   |   |   | J/Q=J''' |
| K |   | K/L=K' |   | K/O=K'' |   |   |   |   |   |   |   |   |
| L |   |   |   | L/P=L'' |   | L/O=L''' |   |   |   |   |   |   |
| M |   | M/N=M' |   |   |   |   |   |   |   |   |   |   |
| N |   |   | N/O=N' |   |   |   |   |   |   |   |   |   |
| O |   | O/P=O' |   |   |   |   |   |   |   |   |   |   |
| P |   |   |   |   |   |   |   |   |   |   |   |   |

FIG. 13

|    | T1 | T2    | T3     | T4     | T5    | T6     | T7     | T8     | T9     |
|----|----|-------|--------|--------|-------|--------|--------|--------|--------|
| A  |    | A/B=A'|        | A/E=A''|       | A/F=A'''|       |        |        |
| B  |    |       | B/C=B' | B/F=B''|       |        |        |        |        |
| C  |    | C/D=C'|        | C/G=C''|       | C/F=C'''|       |        |        |        |
| D  |    |       |        | D/H=D''|       |        | D/G=D'''|      |        |
| E  |    | E/F=E'|        |        | E/I=E''|       |        |        |        |
| F  |    |       | F/G=F' |        | F/J=F''|       |        |        |        |
| G  |    | G/H=G'|        |        | G/K=G''|       |        |        |        |
| H  |    |       |        |        | H/L=H''|       |        |        |        |
| I  |    | I/J=I'|        | I/M=I''|       | I/F=I'''|       |        |        |
| J  |    |       | J/K=J' | J/N=J''|       |        |        |        |        |
| K  |    | K/L=K'|        | K/O=K''|       | K/F=K'''|       |        |        |
| L  |    |       |        | L/P=L''|       |        | L/G=L'''|      |        |
| M  |    | M/N=M'|        |        |       |        |        | M/J=M'''|       |
| N  |    |       | N/O=N' |        |       |        |        |        |        |
| O  |    | O/P=O'|        |        |       |        |        | O/J=O'''|       |
| P  |    |       |        |        |       |        |        |        | P/K=P'''|

FIG. 15

VIDEO PROCESSING METHODS FOR IMPROVING VISUAL ACUITY AND/OR PERCEIVED IMAGE RESOLUTION

CROSS-REFERENCE TO RELATED APPLICATION(S)

This application is a divisional of U.S. application Ser. No. 11/115,620, filed Apr. 27, 2005, now U.S. Pat. No. 7,266,413 which is a divisional of U.S. application Ser. No. 09/851,268, filed May 7, 2001, now U.S. Pat. No. 6,920,358 which claims the benefit of U.S. Provisional Application No. 60/207,529, filed May 26, 2000.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to visual, e.g., video, processing techniques and is of particular use in conjunction with an implantable medical device, e.g., a retinal prosthesis, for improving visual acuity.

BACKGROUND OF THE INVENTION

Various conditions, e.g., age-related macular degeneration, retinitis pigmentosa, etc., exist which effect the functioning of photoreceptors (i.e., rods and cones) on a patient's retina and thus eliminate or severely degrade the patient's vision. To overcome these conditions, it has been proposed to directly stimulate the visual cortex (see for example, Bindley G, Lewin W. The sensations produced by electrical stimulation of the visual cortex. J. Physiol (London) 1968:196:479-493) or to implant a retinal prosthesis to stimulate neural pathways within a patient's retina (see for example, U.S. Pat. No. 4,628, 933 to Michelson and U.S. Pat. No. 5,935,155 to Humayun et al.). Each of these approaches potentially suffer from resolution problems in that the various mechanical, electro-mechanical, thermal and other technological limitations may, within the foreseeable future, significantly limit the resolution of an image that can be imparted to the patient's brain. For example, while a normal retina's resolution may be in the order of 4,000,000 pixels (picture elements), and the resolution of a computer screen (or compatible charge-coupled device (CCD) video camera) is of the order of 1,000,000 pixels, a reasonable goal for the aforementioned technologies may be 1,000 pixels. Accordingly, the visual acuity would potentially be degraded by a factor of at least 1,000 (still a significant benefit for patients in need of such devices). In some of the aforementioned devices, e.g., the Michelson device, there is a direct one-to-one relationship between each video processing component, e.g., CCD element, and the electrode that stimulates the retina (see FIG. 6), while in other devices, e.g., the Humayun et al. device, this relationship is not expressly discussed.

Additionally, it has been observed that normal eyes periodically jitter, i.e., they are subject to fast movements of the eyes separated by fixation periods during which the eyes are relatively still. While such eye movements (also referred to as saccadic eye movements) may represent vestigial physiological features that are overcome by processing in the patient's brain, some people believe that this saccadic movement actually increases the perceived resolution of the visual image beyond that which could otherwise be achieved solely based on the retinal photoreceptor density.

Accordingly, what is needed are techniques and apparatus for applying such techniques that can obtain the benefits of a "high" resolution video device/signal and process such signal to enhance the perceived visual acuity beyond that of a "low" resolution electrode array.

SUMMARY OF THE INVENTION

The present invention is generally directed to visual, e.g., video, processing techniques and is of particular use in conjunction with an implantable medical device, e.g., a retinal prosthesis, for improving visual acuity. Various conditions, e.g., age-related macular degeneration, retinitis pigmentosa, etc., exist which effect the functioning of photoreceptors (i.e., rods and cones) on a patient's retina and thus eliminate or severely degrade the patient's vision. To overcome these conditions, various apparatus have been proposed to provide vision to such patients. There are three main structures that have been described in the art. In a first structure (referred to herein as a Bindley type apparatus), an input from a video camera is used to stimulate discrete points on the patient's cerebral cortex. In a second structure (referred to herein as a Humayun type apparatus), an input from a video camera is used to stimulate discrete points on a patient's retina. In a third structure (referred to herein as a Michelson type apparatus) optical sensors are supplied in a one-to-one relationship to stimulate discrete points on a patient's retina. Each of these structures potentially suffer from resolution problems that, for the foreseeable future, significantly limit the density of electrodes at the patient's brain or retina that may stimulated and thus limit the resolution of an image that can be imparted to the patient's brain. The present invention recognizes that a video input, e.g., from a video camera, provides a signal of "higher" resolution (e.g., 1,000,000 or more pixels) that may be processed to supplement a "lower" resolution (e.g., 16 to 10,000 elements) electrode array and thus impart an enhanced image to the patient's brain.

To take advantage of the input signal which has a significantly higher input resolution as compared to the output resolution available for the electrode array (e.g., by a factor of four or more), the present invention discloses various techniques for associating subsets of the pixels available from the input signal to individual output electrodes. Preferably, various techniques may be used to vary this association. These techniques include varying how each subset is processed, e.g., altering between mean and medium processing, and varying the association between the input pixel subset and the output electrodes. These alterations may occur periodically at a predetermined rate, direction, and/or magnitude, e.g., number of pixels, or may occur in a closed loop manner in response to ocular muscle control signals, e.g., to emulate the effects of saccadic eye movement.

A preferred embodiment of an apparatus for increasing perceived visual acuity suitable for use in providing vision to a visually-impaired patient comprises (1) a high resolution optical input device for receiving an optical signal and providing a video signal in response thereto, (2) a video processor for receiving the video signal as an array of input pixels, wherein the video processor selects subsets of the input pixels and processes the selected subsets to determine an output pixel value for each selected subset, (3) a low resolution video output device for responding to an electrical signal to generate a pixelated image, the pixelated image having a resolution of no more than one fourth of the image resolution available from the high resolution optical input device, and (4) a display driver providing electrical signals for driving pixels in the low resolution video output device in response to the output pixel values from the video processor. In a further aspect of a preferred embodiment, the low resolution video output device is a retinal prosthesis for stimulating neural pathways, e.g., ganglion or bipolar cells, in the patient's retina.

In a still further aspect of a preferred embodiment, the video processor periodically alters its processing algorithm for associating input pixel subsets to output pixels. Such alterations include fixed alteration patterns, pseudo-random alteration patterns and alterations and/or alteration patterns determined by a patient input device, e.g., by the patient or a physician as part of a patient fitting operation. Furthermore, such alteration may be done in a closed loop manner in response to signals from a neural sensor which senses movement of a patient's eye to generate an eye movement signal and wherein the video processor periodically alters the selected pixels in each subset in synchronization with the sensed eye movement signal.

In an additional aspect of the present invention, e.g., for use with an array of retinal or cortical stimulation electrodes, the perceived resolution may be increased beyond that of the physical stimulation electrode array by stimulating combinations of two or more neighboring stimulation electrodes to create virtual electrodes at locations physically displaced from the stimulation electrodes. Such a feature may be used independently to increase visual acuity or in conjunction with the aforementioned subsetting embodiments to result in a further benefit.

The novel features of the invention are set forth with particularity in the appended claims. The invention will be best understood from the following description when read in conjunction with the accompanying drawings.

BRIEF DESCRIPTION OF THE DRAWINGS

FIGS. 4A-4C illustrate examples of how altering alignment effects viewing a limited resolution image.

FIG. 5A-5C illustrate examples of how altering alignment effects viewing a limited resolution image.

FIG. 11 is a simplified diagram of the coordinated stimulation of neighboring physical electrodes to result in a virtual electrode located in-between.

FIG. 12 is an exemplary electrode array that is stimulated in neighboring electrode pairs to result in a plurality of virtual electrode sites in-between.

FIG. 13 is a chart of an exemplary stimulation pattern for stimulating the physical electrodes of FIG. 12 to result in a plurality of virtual electrode sites in-between.

FIG. 14 is an alternative exemplary electrode array that is stimulated in neighboring electrode pairs to result in a plurality of virtual electrode sites in-between.

FIG. 15 is a chart of an exemplary stimulation pattern for stimulating the physical electrodes of FIG. 14 to result in a plurality of virtual electrode sites in-between.

DETAILED DESCRIPTION OF THE PREFERRED EMBODIMENTS

Figure 1:
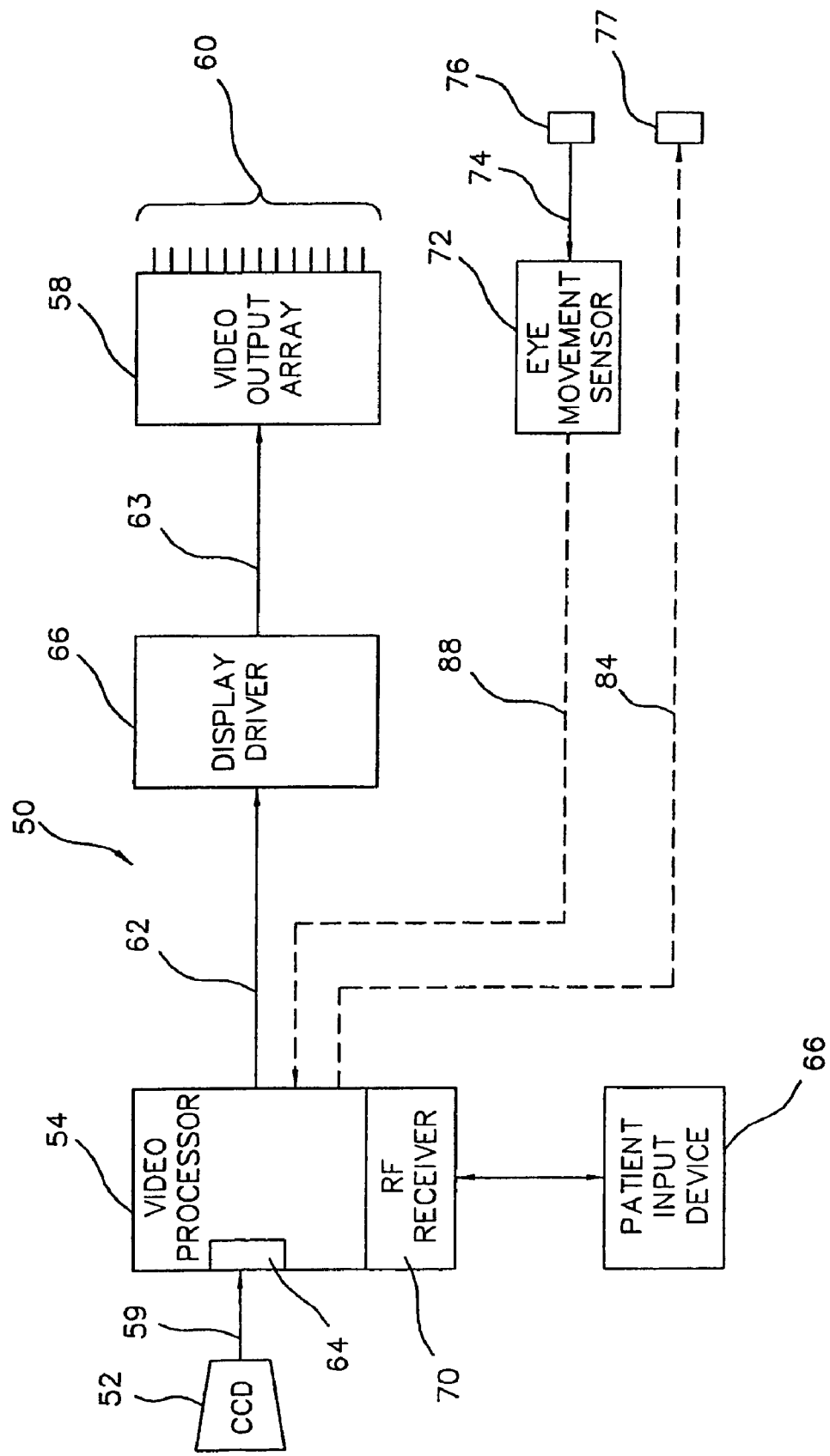
FIG. 1 is a simplified block diagram of an exemplary embodiment of the present invention for associating subsets of pixels from a "high" resolution input video device to a "low" resolution video output device.

The following description is of the best mode presently contemplated for carrying out the invention. This description is not to be taken in a limiting sense, but is made merely for the purpose of describing the general principles of the invention. The scope of the invention should be determined with reference to the claims.

The present invention is generally directed to visual, e.g., video, processing techniques and is of particular use in conjunction with an implantable medical device, e.g., a retinal prosthesis, for improving visual acuity. Various conditions, e.g., age-related macular degeneration, retinitis pigmentosa, etc., exist which effect the functioning of photoreceptors (i.e., rods and cones) on a patient's retina and thus eliminate or severely degrade the patient's vision. To overcome these conditions, various apparatus have been proposed to provide vision to such patients. There are three main structures that have been described in the art. In a first structure (referred to herein as a Bindley type apparatus), an input from a video camera is used to stimulate discrete points on the patient's cerebral cortex. In a second structure (referred to herein as a Humayun type apparatus), an input from a video camera is used to stimulate discrete points on a patient's retina. In a third structure (referred to herein as a Michelson type apparatus) optical sensors are supplied in a one-to-one relationship to stimulate discrete points on a patient's retina. Each of these structures potentially suffer from resolution problems that, for the foreseeable future, significantly limit the density of electrodes at the patient's brain or retina that may stimulated and thus limit the resolution of an image that can be imparted to the patient's brain. The present invention recognizes that a video input, e.g., from a video camera, provides a signal of "higher" resolution (e.g., 10,000-1,000,000 or more pixels) that may be processed to supplement a "lower" resolution (e.g., 16 to 10,000 elements) electrode array and thus impart an enhanced image to the patient's brain.

To take advantage of the input signal which has a significantly higher input resolution as compared to the output resolution available for the electrode array (e.g., by a factor of four or more), the present invention discloses various techniques for associating subsets of the pixels available from the input signal to individual output electrodes. Preferably, various techniques may be used to vary this association. These techniques include varying how each subset is processed, e.g., altering between mean and medium processing, and varying the association between the input pixel subset and the output electrodes. These alterations may occur periodically at a predetermined rate, direction, and/or magnitude, e.g., number of pixels, or may occur in a closed loop manner in response to ocular muscle control signals, e.g., to emulate the effects of saccadic eye movement.

While the present invention is applicable to multiple prosthetic environments, the following description is primarily directed to a particular exemplary environment, e.g., using a Humayun type apparatus, wherein a video camera is the high resolution input device that provides an input to a video processor which in turn outputs stimulation signals, e.g., via a display driver, to an electrode array proximate to the patient's retina. However, one of ordinary skill in the art will readily recognize that the present invention is not limited to use with such an apparatus and that the scope of the present invention is determined by the functions and algorithms practiced by embodiments of the present invention and is not limited by the physical partitioning of the blocks which implement these functions nor the choice and/or location of the stimulation electrode array, e.g., as a retinal or a cortical prosthesis.

As shown in FIG. 1, an exemplary embodiment 50 of the present invention is primarily comprised of a (1) a "high" resolution video input device 52, (2) a video processor 54, (3) a display driver 56, and (4) a "low" resolution video output array 58. In a preferred embodiment, the "high" resolution input device 52, e.g., a CCD (charge coupled device) camera or equivalent, provides a video signal 59 that is typically of the order of 10,000-1,000,000 or more pixels of resolution. Also, in a preferred embodiment, the "low" resolution output array 58 is a retinal prosthesis comprised of an electrode array 60 that is capable of stimulating neural pathways, e.g., ganglion or bipolar cells at the patient's retina, and thus provides perceivable visual information, i.e., phosphenes, to the patient's brain. Typically, and for the foreseeable future, due to various mechanical, electro-mechanical, thermal and other technological limitations, the electrode array may be limited to be of the order of 1,000 stimulation sites which are capable of generating a perceivable image of 1,000 pixels. Due to this exemplary resolution discrepancy, a 10-1,000 fold visual acuity degradation would be anticipated without the present invention (still a significant benefit for a patient in need of such a device). However, the present invention uses the video processor 54 to assign pixel subsets from the video signal 59 to individual electrodes within the electrode array 60 in the retinal prosthesis. By varying the criteria for this subsetting, it is believed that the patient may perceive additional visual information, e.g., clues, that will enhance the perceived visual image beyond that directly corresponding to the resolution of the video output array 58. Additionally, it is recognized that this description refers to an exemplary implementation. Accordingly, the resolution of the video input device 52 may be increased or, for cost reasons, decreased, while the resolution of the electrode array 60 is expected to increase as the technology permits. However, as long as there is a significant resolution discrepancy, e.g., a factor of four or more, the present invention may be used to enhance the patient's perceived visual acuity.

The video processor 54 generates a processed pixel subset signal 62 that is coupled to the display driver 56 which drives the discrete electrodes in the electrode array 60 of the retinal prosthesis. Typically, the display driver 56, provides a biphasic signal via path 63 to each electrode in the electrode array 60 to optimize the electrode/neural interface. However, delivery of a monophasic capacitively coupled signal to the neural interface is also known in the art and is considered to be within the scope of embodiments of the present invention.

Figure 2:
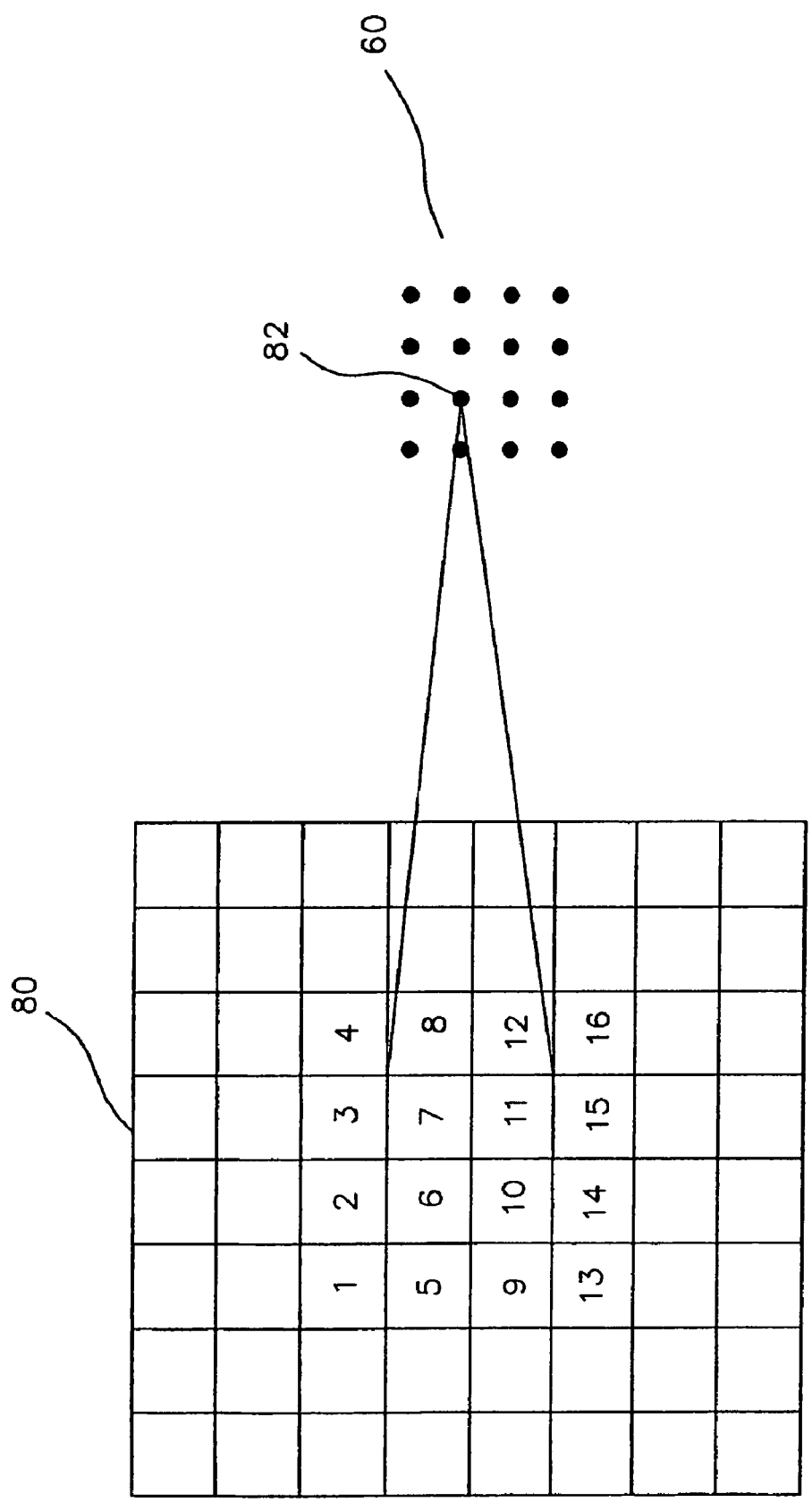
FIG. 2 is a simplified example of varying the subsetting of input pixels to alter their association with output pixels.

In embodiments of the present invention, a plurality of pixels from the video input device 52 are assigned as a subset to each output electrode of the electrode array 60. Preferably, this subsetting is varied, as shown in FIG. 2, according to one or more techniques. In FIG. 2, a portion (8×8) of a pixelated image 80 is shown as captured by the video processor 54 and is processed to drive electrodes in a portion (4×4) of the electrode array 60. Initially, in a first exemplary variation, input pixels 6, 7, 10 and 11 form a subset corresponding to output electrode 82. Various algorithms may be used to associate the pixels in each subset to its corresponding output electrode. For example, a value, e.g., a digital value, may be retrieved for each input pixel and the average or the mean of these input pixel values may be calculated and each of these processed values may be used to drive its corresponding output electrode. In another variation, all of the input pixel values may be processed to determine the minimum and maximum value of the video signal 59 and the input pixel values may be scaled to vary the range of input pixel values, e.g., according to a logarithmic scale or to otherwise provide an automatic gain control function. After this scaling process is completed and a subset of scaled input pixels is assigned to each output pixel, each of the scaled input pixel subsets is processed and used to drive its corresponding output pixel, e.g., electrode.

Figure 3:
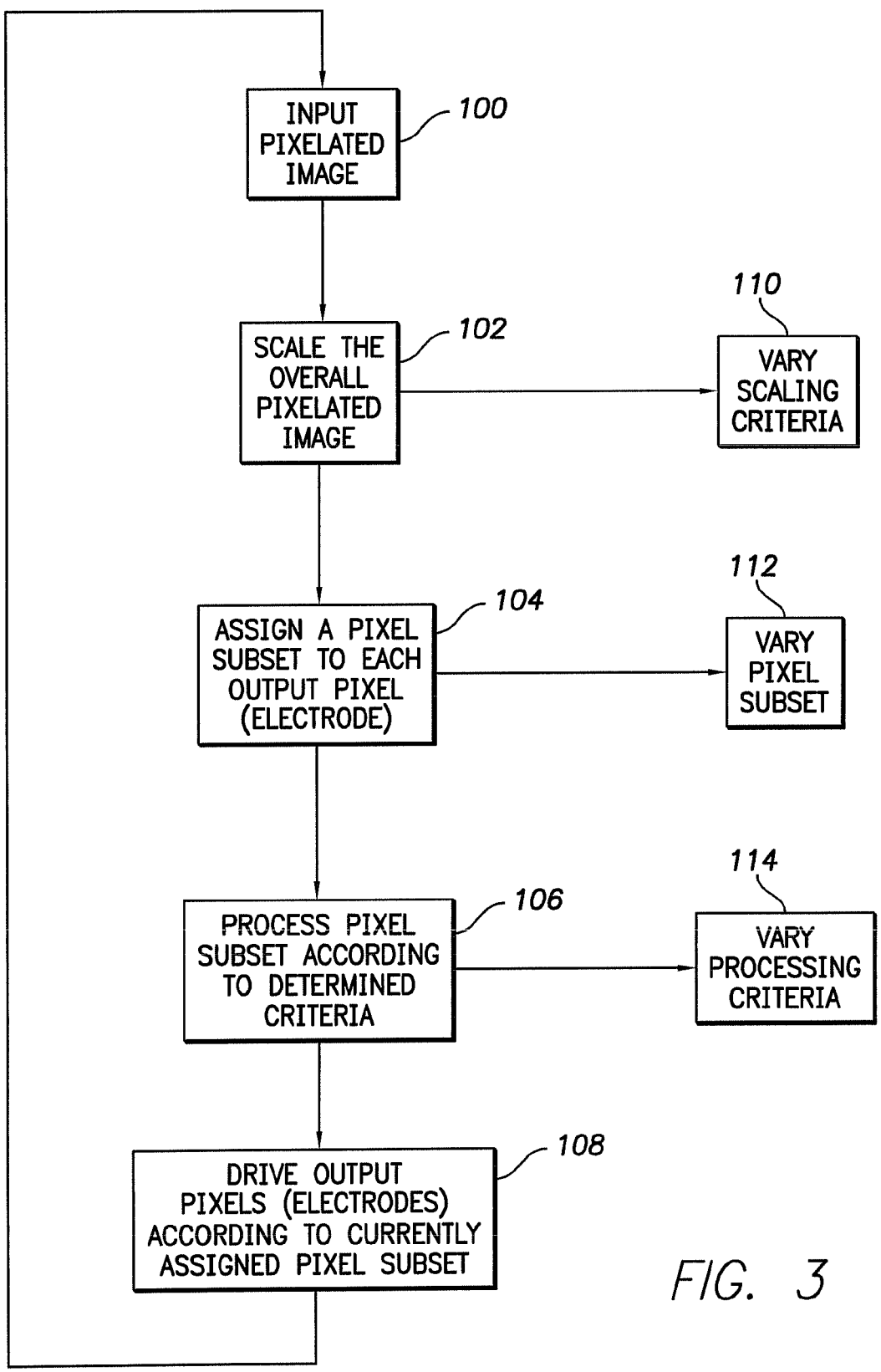
FIG. 3 is a simplified flow chart of a method exemplary of the present invention for associating subsets of pixels from a "high" resolution input video device to a "low" resolution video output device.

A simplified flow chart of such a process is shown in FIG. 3. The process is preferably performed by a microcontroller or the like (not shown) within the video processor 54. However, the use of a special purpose A/D (analog to digital converter) or other video processing logic with or without an additional microcontroller are all design choices within the scope of the present invention. Periodically, in block 100, a pixelated image is input from the input video device 52 via video signal 59 to a pixel memory 64 (see FIG. 1). Preferably, in block 102, the overall pixelated image is scaled and, in block 104, a subset of the scaled pixelated image is assigned to each output electrode. Then, in block 106, each input pixel subset is processed according to a defined criteria and, in block 108, the corresponding output electrodes are driven according to the processed pixel subset. The process then continues and repeats at step 100. While one might infer from this simplified flow chart that there is a one-to-one relationship between the inputting of the pixelated image in block 100 and the driving of the output electrodes in block 108, this may not always be the case. For example, in some cases it may be necessary to stimulate the ganglion or bipolar cells in block 108 at a higher refresh rate (to avoid the patient perceiving flickering or other detrimental effects in the perceived image) than may be achieved from blocks 100-104 (due to hardware or software limitations). In such cases, block 108 would be an independent, parallel process (preferably, with some synchronization to avoid outputting signals to the electrodes while the output pixelated image is being updated) as would be understood by one of ordinary skill in the art.

Additionally, it may be desirable to periodically alter the selection of input pixels which form each subset in a manner somewhat analogous to that of the eye's saccadic movement. (The purpose of this alteration will be discussed further below). Referring again to FIG. 2, the "initial" subset of input pixels 6, 7, 10, 11 may periodically change upwards to input pixels 2, 3, 6, 7, downwards to input pixels 10, 11, 14, 15, right to input pixels 7, 8, 11, 12, or left to input pixels 5, 6, 9, 10. There are multiple potential purposes of such an alteration. First, some individuals believe that saccadic eye movements are used by the patient's brain to improve visual acuity. Accordingly, by emulating this biological jittering process, i.e., saccadic movement, it is theorized that the perceived visual image may be increased. There are multiple techniques for duplicating this process. First, this jittering process, i.e., altering the input pixel subset associated with each output electrode, can be performed in an open loop manner according to a fixed or pseudo-random subsetting pattern. It is believed that the patient's brain may be able to detect these alterations and use these jittered images to supplement each other and thereby improve visual acuity. In alternate techniques, this jittering can be done in a closed loop manner. In a first preferred closed loop technique, an eye movement sensor 72 senses an electrical signal 74, e.g., an extraocular muscle signal or the like from a cuff electrode 76, a video camera pointed at the eye, an infrared sensor, etc., to generate an eye movement signal 78 and this eye movement signal is used to instruct the video processor 54 to jitter the selected input pixels in each subset. Such a cuff electrode may be positioned to measure a signal from the patient's brain (measuring the intended eye movement), anywhere along the neural pathway to the eye muscles (also, measuring the intended eye movement), at the eye muscles (measuring the actual depolarization of the eye muscles), anywhere along a feedback neural pathway that senses eye movement, or an eye tracking system (actually measuring the eye movement). Any such signal is considered to be a sensed eye movement signal. In an alternative closed loop technique, the video processor 54 outputs a neural signal 84, e.g., to cuff electrode 77, in synchronization to its generated jitter movement and to thus inform the patient's brain when each jitter movement occurred.

Even if, in fact, saccadic eye movement, was a vestigial artifact, jittering, e.g., open loop jittering, may still be used to increase visual acuity by periodically altering the association of input pixel subsets to the output pixels, e.g., electrodes. As discussed further below, this jittering effectively causes quantization/sampling type alteration signals that may provide visual queues to the patient.

In a further variation, eye movement may be measured to determine values corresponding to its frequency and/or amplitude and these measured statistical values may be used to determine the frequency and/or the amplitude of the jittering processing performed by the video processor 54.

Finally, it has already been discussed that it is preferable that the pixelated input image be scaled before processing. In a similar manner, it may be preferable that subsetting may be altered in response to data within the pixelated image that correspond to useful data transitions, e.g., edges (black and white and/or color) within the input image. By periodically altering the subsets according to the detected data transitions, i.e., by jittering the processed pixelated image accordingly, improved visual cues will be provided to the patient and thus the perceived visual acuity will be improved. This function may be facilitated when an input color video signal is available. For example, it may be desirable to process a color video signal, e.g., from a color video camera, to look for color dependent data transitions even if the output pixel pattern (due to display driver limitations) may be monochromatic. However, the additional color input information may still be used to facilitate recognizing edges of the input image beyond that achievable by intensity level detection in an input monochromatic image.

The decision as to how, when and what to vary to improve the visual acuity to the patient with the disclosed device is preferably enhanced by an interface to a patient input device 66 via interface path 68, e.g., an RF interface. Preferably, in a manner somewhat analogous to a cochlear implant or a hearing aid, the ability to provide a useful function for an individual patient and/or a particular environment may require different settings. Accordingly, the patient input device 66 may be used to alter the stimulation signals provided by the display driver 56 to the electrode array 60 (preferably via a common RF receiver 70). More significantly, in embodiments of the present invention, the patient input device 66 (preferably via manual inputs) alters the functioning of the video processor 54. Some of these potential alterations are shown in the additional blocks of the flow chart of FIG. 3, each of which may be altered via instructions from the patient input device 66. Block 110 instructs block 102 to vary the overall scaling criteria, e.g., the contrast. For example, when reading text, the overall scaling criteria would preferably be different than that used for recognizing a person's face. Such a selection is somewhat analogous to a selection done for a hearing aid when speech needs to be detected in a noisy versus a quiet environment, i.e., the scaling criteria preferably change.

Block 112 instructs block 104 to vary the pixel subsetting criteria. Such a function may be changed periodically, i.e., to cause jittering and thus to enhance the ability of a patient to perceive edge transitions. Preferably block 112 also controls the rate of the pixel subsetting variances and the magnitude of the variances, i.e., whether one or more pixels are shifted between subsets on each jitter. Furthermore, the direction of the variances may be altered, e.g., whether the jitter occurs only horizontally, only vertically, or both. Additionally, the order and/or the rate of the variances may be altered, e.g., whether the variances occur in a fixed alteration pattern or following a pseudo-random pattern.

Block 114 instructs block 106 to vary the processing criteria. Such a function can be used to vary whether the mean or the median, or other criteria may be used to increase visual perception.

While the patient input device 66 may be used to directly instruct the video processor 54 to alter its operation in real time, it is preferable, that the patient input device 66 be used to configure the video processor 54 to operate according to different operation modes. Accordingly, the patient input device 66 is preferably only used to instruct the video processor 54 to change operational modes, after which the video processor 54 may be operated in a self sufficient manner.

This aforedescribed resolution enhancement is best seen through an example. Imagine a patient with a 64 electrode array (8×8) looking at a game of checkers. The amount of information that can be presented at a single instance is only 64 image pixels. If only the average value of squares in the 8×8 grid is available, the patient could see the board itself. However, information about the checkers that are on the board might not be seen. Additionally, if the patient moved his/her head slightly, using this same average value would blur the squares together and make the squares indistinguishable. This is displayed in the left column of FIG. 4. At the top is the original image. FIG. 4A is the average light intensity of each square. It can be seen that the checkers in the middle of the squares cannot be distinguished at this point. FIG. 4B represents the problem if the edges of the image pixel do not align with the edges of the camera pixel. Since each of the boundaries is in the middle of the pixels, the light intensity from both of these sides is combined into a single pixel. This has the effect of blurring the image. FIG. 4C further illustrates this problem, since the boundaries are in the center of each pixel.

In an exemplary implementation of the present invention, two stages of image processing are applied to overcome this limitation. In the first stage, processing occurs through a plurality of image subsetting and image transformation filters. The primary goal of this stage is to enhance the image while reducing the number of pixels. The number of pixels is not necessarily reduced to the number of individual electrodes at this stage.

In the second stage, a continuously controlled map, in which the map describes the calculation of the electrode stimulation parameters from the image pixels, is used to generate the electrode stimulation parameters. The electrical currents described by these parameters are presented to the retina. The control of the map could be achieved through saccadic eye movements or a computer generated pattern. This stage is used to increase the acuity of the vision beyond that which would be generated using a stagnant or stoic map of image pixels to electrode parameters. By slightly moving this map over an image, a slightly different image is presented. This motion-presents the information from a slightly different locations of the image for the different instances in time.

Illustrated by the example, the first stage of processing looks to distinguish the pieces from the board and the white squares from the black. This information is maintained while the number of pixels in the image are reduced. The number of pixels could be reduced, in this instance, to a 24×24 grid. This process is necessary to distinguish the boundaries which are used in the subsequent stage.

Using the image that is now at a lower resolution, the image (24×24) is converted into nine consecutive 8×8 pictures. The hashed lines in the original top image display the 24×24 grid that is used. Each small square in the checkerboard is divided into 9 smaller square (3×3). Only one ninth of the information of the checkerboard of the 24×24 image is presented at one instance. However, in nine consecutive stimulations, all of the information could be presented. Restated, a series of 8×8 pictures is displayed. This is the limit prescribed by the number of electrodes. However, since the pixels from which the electrode value is calculated from changes at each instance, more information is presented. This produces the greater acuity.

Examples of these 8×8 pictures are seen in the right column. Explicitly described, FIG. 5A is the value of the top left corner of the 24×24 grid. FIG. 5B is the picture of the center of each 3×3 grid within the larger 8×8 grid. FIG. 5C is the lower right corner. This technique time division multiplexes the information from an image or video to the eye.

Two major problems are overcome through using this technique. The first problem is that information from an image's pixels is blurred together to produce one precept. This technique displays a greater number of electrode pixels than the physical number of electrode pixels by changing the pixels that are used in each instance in time. This allows the patient to receive more information. The second problem is the alignment. Since the pixels are taken from slightly different positions at each instance in time, the patient will not face the problem that the image pixels obscure or blur boundaries of objects together into one pixel. The patient will instead see that there are two (or multiple) values that are within the same area. This is a key element in recognizing that boundaries do exist.

The first stage of filtering enhances the image while reducing the number of pixels, and the second stage presents the image in a manner to increase the acuity of the vision, which is the final goal of this process. The combination of these types of filters maintains the presence and integrity of objects that exist in the video stream while reducing the number of pixels acquired by the camera to the physical number of electrodes. In the first stage, two types of filters are used: image subsetting and image transformation. In the second stage, a filter that converts the image to stimulation parameters is used.

A selection of image processing pathways allows each pathway to be adjusted. This, in turn, can maximize each filter pathways effectiveness in particular situations. Specific filters, such as object recognition, may be used for an individual who is navigating in an environment. Increased acuity filters, such as the scanning or saccadic filters, may be used to assist reading of characters and fine detail recognition. Optimizations, such as maximum object recognition, contrast, image stabilization, or motion detection may be employed.

As previously described, different embodiments of the image processing path may be selected by the patient. This selection could be a selection of a specific image processing path, or an optimization method. Hierarchically beneath this level of patient control, the video processor 54 may continuously adjust the image to maintain the particular optimization. The selection of the filter can allow for the patient to prescribe the image quality and produce a suitable image processing path.

This technique expands descriptions of the mapping of pixel values to electrode stimulation parameters. Known prior art devices imply the use of a static or selectable static mapping. This technique encompasses a continuously adjustable mapping, where the continuous adjustment could be derived from the motion of the eye, mimicking saccadic eye movements, or fixed or random patterns calculated. This technique increases the acuity of the image that is produced in the retina by automatically and continuously controlling and/or altering the map of the location.

This technique may also include tracking of the motion of the eye and selecting portions of the video image to be used for calculation of the electrode stimulation parameters. The motion of the eye may be interpreted as translations of the video image. The eye movement may be monitored and the image translated according to the monitored eye movement. The translations of the image are physically realized by changes in the information presented to the retina. This technique is not limited to mechanical monitoring of the eye. For example, by sensing EOG signals, i.e., electrical signals from extraocular muscles, one may detect eye movement. Alternatively, the tracking of the eye may be done through mapping afferent electrical signals from the optic nerve. The optic nerve innervates and controls the activity of the muscles connected to the eye, and in turn the movement of the eye. As a corollary, the efferent neurons from the muscles of the eye may be stimulated in conjunction with the slight movement of the continuously adjustable mapping to coordinate the movement of the image with respect to the eye and efferent feedback from the muscles of the eye.

Figure 6:
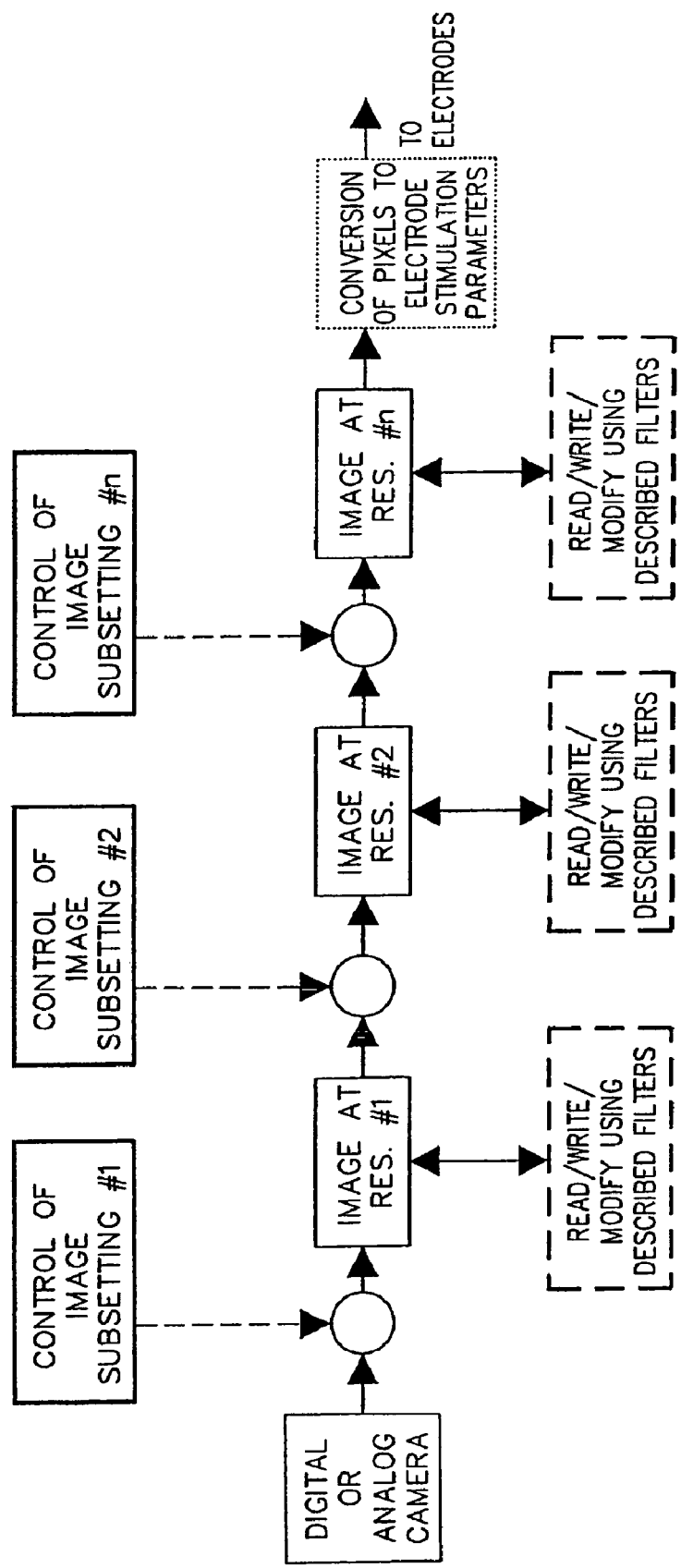
FIG. 6 is a simplified exemplary block diagram of the image processing pathway.
Figure 7A:
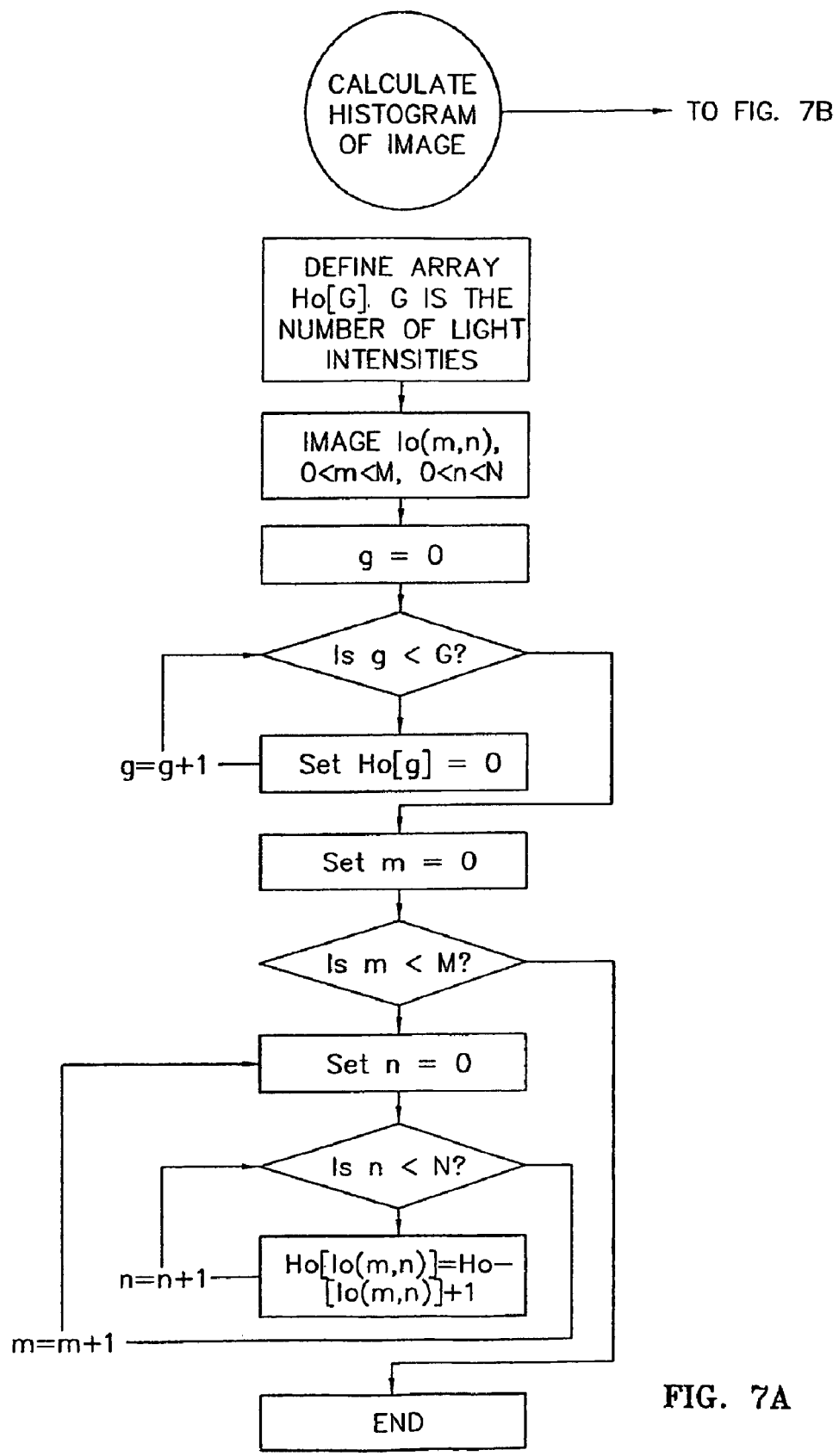
FIGS. 7A-7E comprise a simplified exemplary flow chart of histogram mapping.
Figure 7B:
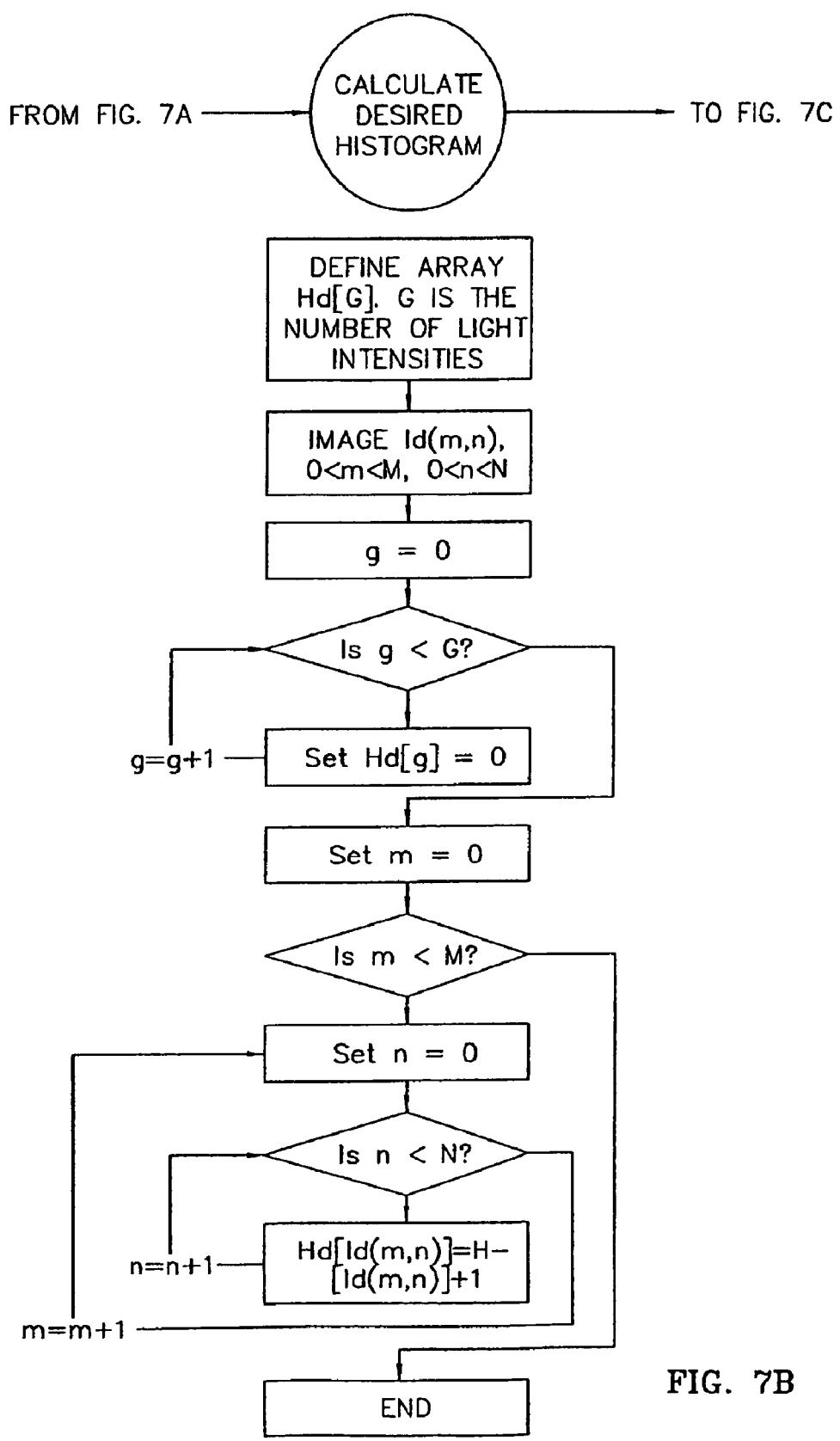
Figure 7C:
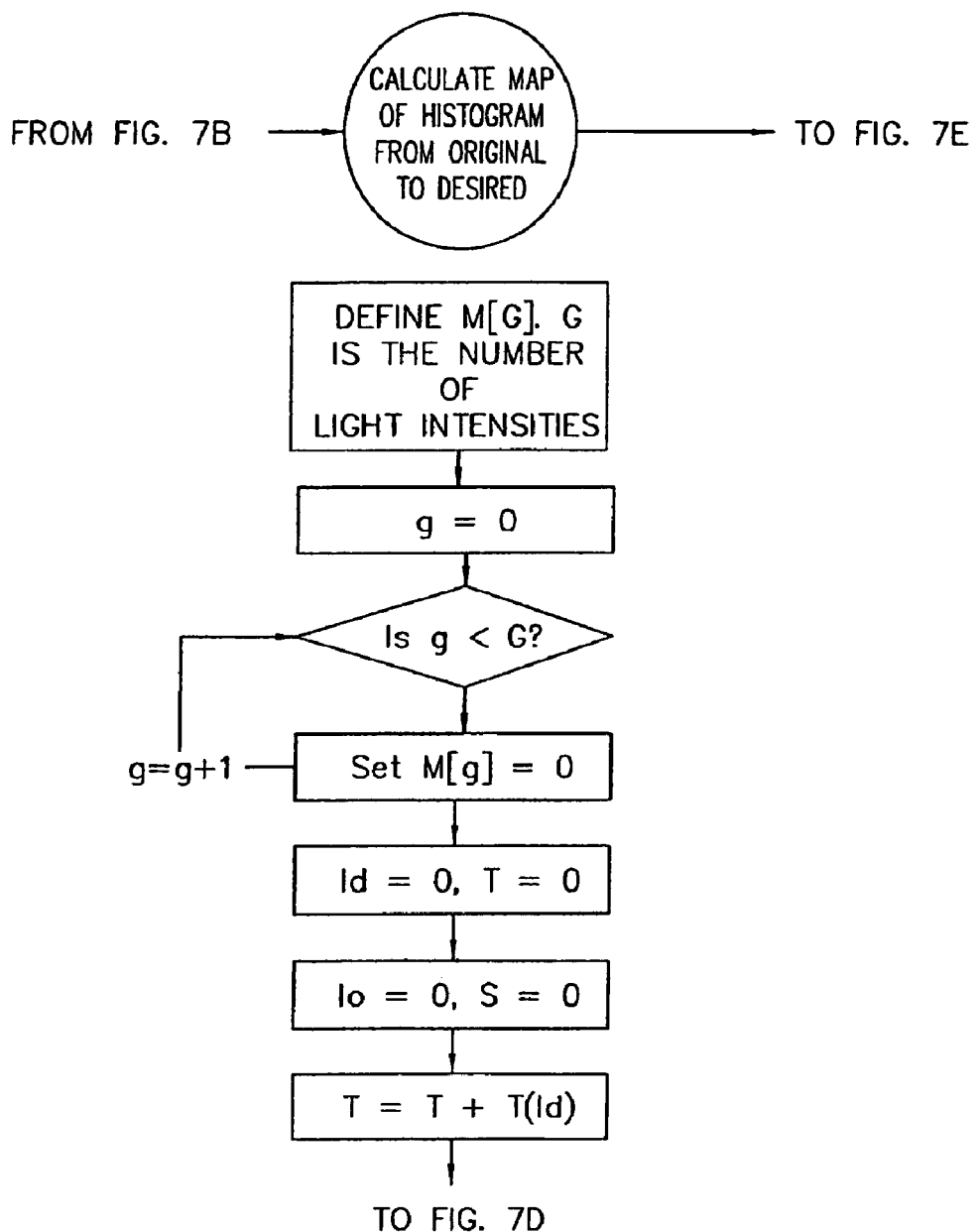
Figure 7D:
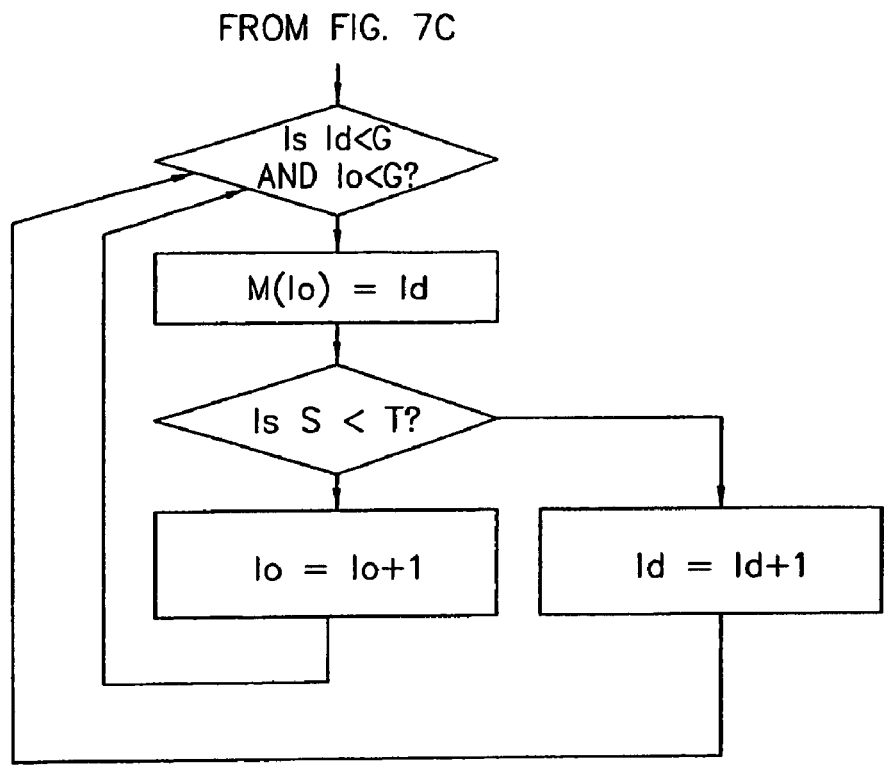
Figure 7E:
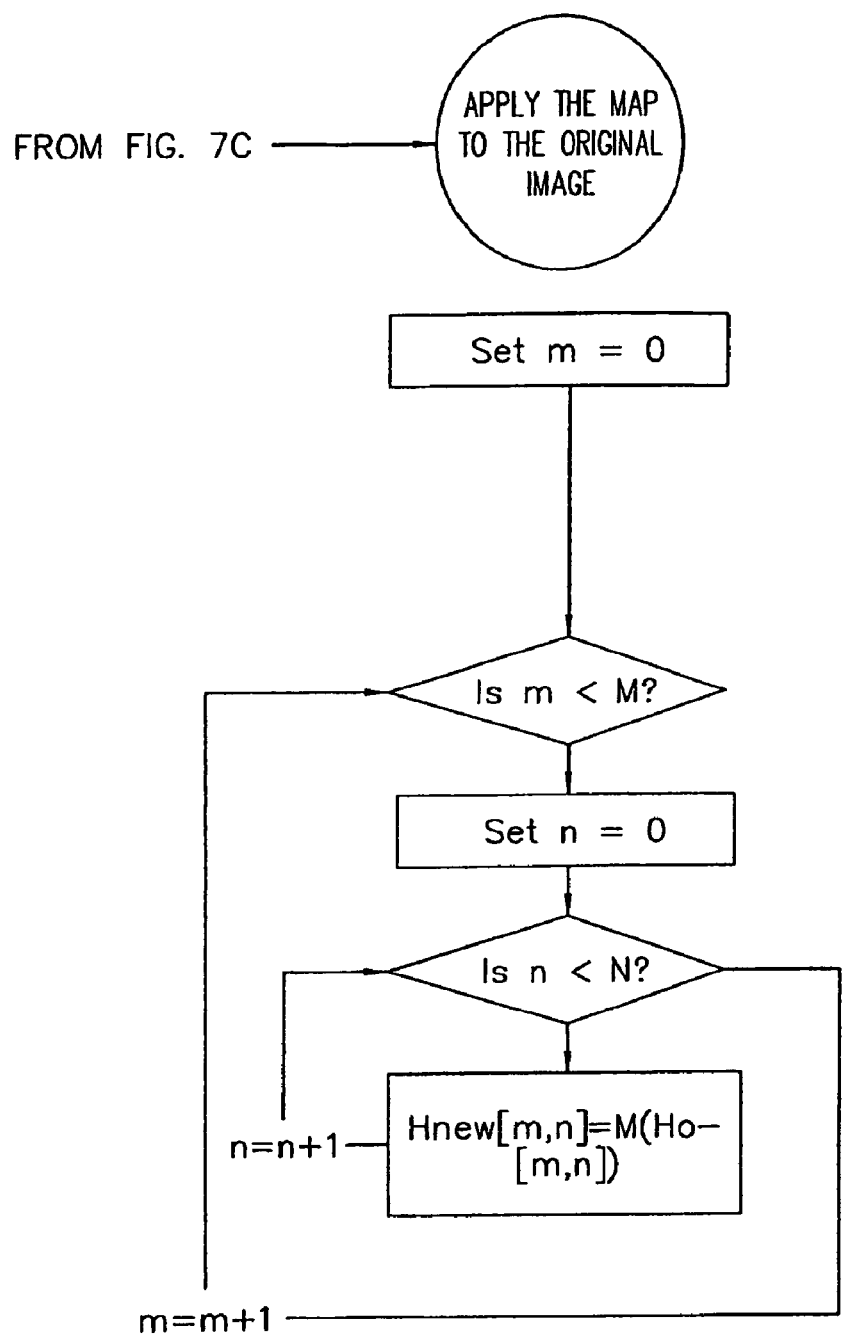

The image processing pipeline is essentially a selection of these types of image processing. The overall diagram is shown in FIG. 6. The image processing algorithms use a digital video image from a source (e.g., video input device 52) and apply a plurality of filters to the image to derive the electrode stimulation parameters. Particular image processing functions (e.g., cropping, zoom, resizing, subsetting) may take place in the analog image prior to its conversion to a digital image. These image processing functions are available through analog video to digital video converter chips, e.g., Phillips SAA7114. The use of such a special purpose chip, may be desired to offset the digital computation requirements for a microcontroller or the like in the video processor 54. However, the choice of whether to process the video as an analog or digital signal and whether to process digital signals in special purpose hardware versus software are all considered to be design choices that are within the scope of the present invention.

In order to provide the implanted patient with a better quality image perception, digital image processing techniques are preferably used. This increases and enhances the visual acuity within the image. These image processing techniques can be classified into three types. The first type is read/modify write operations that occur on an image, i.e., from filtering. These are diagramed in the dashed outlined boxes. The second type is a subsetting filter which changes the number of pixels that display the image. These operators are diagramed in the solid outlined boxes. The third type of filter is the conversion of the image to a set of electrode stimulation parameters. This filter is diagrammed as the dotted box.

The choice and combinations of the subsetting, filtering, and conversion to stimulation parameters are made to display the best image on the retina. This involves the selection of appropriate subsetting filter methods and filtering methods that are necessary for maintaining the integrity of the objects of an image (as a still frame of moving video) in a lower resolution display.

The following types of filters (or combinations thereof) may be used:
1) histogram mapping
2) contrast and brightness filters
3) kernel filters—edge enhancement
4) automatic or manual repositioning of the image
5) object recognition—detection
6) image cropping
7) image zoom
8) image resizing
9) image subsetting
10) automatic or manual setting and resetting the map used to calculate electrode stimulation parameters from the image pixels.

Within each of the defined boxes, one or more than one filter may be used.

Image Processing Background

A digital image consists of picture elements (pixels) that have a defined light intensity (grayscale) or color. Each of the pixels has a location, which can be described by a two dimensional co-ordinate system. Each pixel also has a color or grayscale, which is represented by a number. The image can be represented as a matrix of those grayscales where M and N are the dimensions of the image and $I_{max}$ is the maximum light intensity of a pixel:

$$I=I[m,n] \; (0 \leq m \leq M-1, 0 \leq n \leq N-1, 0 \leq I \leq I_{max})$$

Image processing techniques can be applied to the image to change the light intensities of individual pixels, change the size of the image, or both. The following are exemplary image processing techniques that may be used in embodiments of the present invention.

For each of the light intensity values that are possible in the original image, the number of occurrences of each light intensity value is recorded. This counting of the number of occurrences can be represented pictorially as a histogram (see FIGS. 7A-7E). This produces a scalar:

$$H_{original}(I_o) = \sum_{n=0}^{N-1} \sum_{m=0}^{M-1} \delta(I[m,n] - I_o) \; \text{where} \; \delta(x) = \begin{cases} 1 \text{ if } x = 0 \\ 0 \text{ if } x \neq 0 \end{cases}$$

A transfer function is derived, $(M(I_o))$, such that:

$$I_d = M(I_o) \Bigg| \sum_{0}^{I_d} H_{desired}(I) = \sum_{0}^{I_o} H_{original}(I)$$

The $M(I_o)$ function is applied to the original image pixels. This changes the pixels intensities to map to a histogram which matches that of the desired image:

$$I_{desired}[m,n] = M(I_{original}[m,n])$$

Contrast and Brightness Filters

For brightness or contrast adjustment, the following technique is used:

$$I_{desired}[m,n] = aI_{original}[m,n] + b \text{ for } 0 \leq m \leq M-1, 0 \leq n \leq N-1$$

This change occurs at every pixel. Restated, for each pixels light intensity level ($I_{old}$), a new light intensity level $I_{new}$ is computed based on the above equation.

If |a|>1, the contrast increases
If |a|<1, the contrast decreases
If a<0, the image is inverted
If b>0, the brightness increases
If b<0, the brightness decreases Kernel Filters Given a pixelated image I[m,n], a kernel filter can be applied of J×K pixels h[j,k] so that the new image o[m,n] is determined by the equation:

$$I_{desired}[m,n] = \sum_{k=0}^{K-1} \sum_{j=0}^{J-1} h[j,k] I_{original}[m-j, n-k]$$
$$= h[j,k] \otimes I_{original}[m,n]$$

Particular filters can enhance the edges of an image such as:

$$h[j,k] = [\,1 \quad -2 \quad 1\,] \text{ which highlights vertical edges}$$

$$h[j,k] = \begin{bmatrix} 1 \\ -2 \\ 1 \end{bmatrix} \text{ which highlights vertical edges}$$

$$h[j,k] = \begin{bmatrix} 2 & -1 & 2 \\ -1 & 4 & -1 \\ 2 & -1 & 2 \end{bmatrix} \text{ which picks out edges in both directions}$$

Figure 8:
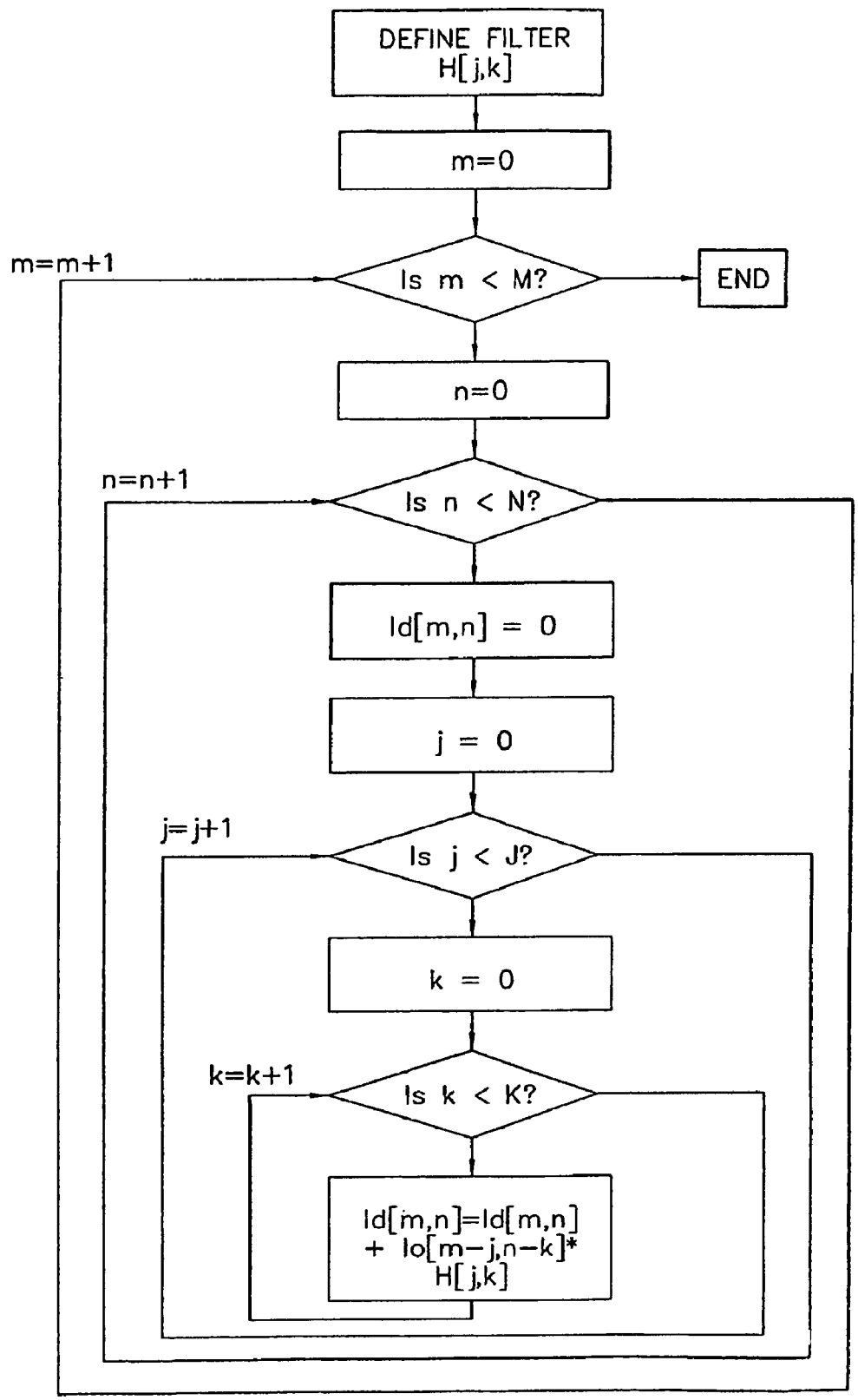
FIG. 8 is a simplified exemplary flow chart of kernel mapping.

A flow chart for the one implementation of a kernel filter is shown in FIG. 8.

Automatic or Manual Translation (Repositioning) of the Image

For an image, a new image may be generated by filtering with the appropriate kernel filter:

$$h[j,k] = \begin{bmatrix} 0 & 0 & 0 \\ 0 & 1 & 0 \\ 0 & 0 & 0 \end{bmatrix} \; (-1 \leq j \leq 1, -1 \leq k \leq 1)$$

which does not change the position of the image. However, $$h[j,k] = \begin{bmatrix} 0 & 1 & 0 \\ 0 & 0 & 0 \\ 0 & 0 & 0 \end{bmatrix} \; (-1 \leq j \leq 1, -1 \leq k \leq 1)$$

will translate the image down one pixel, $$h[j,k] = \begin{bmatrix} 0 & 0 & 0 \\ 0 & 0 & 0 \\ 0 & 1 & 0 \end{bmatrix} \; (-1 \leq j \leq 1, -1 \leq k \leq 1)$$

will translate the image up one pixel, $$h[j,k] = \begin{bmatrix} 0 & 0 & 0 \\ 1 & 0 & 0 \\ 0 & 0 & 0 \end{bmatrix} (-1 \leq j \leq 1, -1 \leq k \leq 1)$$

will translate the image to the right one pixel, and $$h[j,k] = \begin{bmatrix} 0 & 0 & 0 \\ 0 & 0 & 1 \\ 0 & 0 & 0 \end{bmatrix} (-1 \leq j \leq 1, -1 \leq k \leq 1)$$

will translate the image to the left one pixel.

Object Recognition/Detection

It might be necessary to resize individual objects within a scene without resizing an entire object. This could be done if the object could be identified in the scene. To identify objects in the scene, the following types of algorithms can be used. Essentially, these algorithms:

1) calculate an intermediate image by replacing the luminosity of each pixel with the maximum or minimum value of each pixel and each of its neighbors
2) calculate a new image by subtracting the original image from the intermediate image This leaves only an outline of objects that within an image which may be represented by the equation:

$$I_{Intermediate}[m,n] = \max(I_{original}[m-j,n-k] \otimes b[j,k])$$

where:

$$b[j,k] = \begin{bmatrix} 0 & 1 & 0 \\ 1 & 0 & 1 \\ 0 & 1 & 0 \end{bmatrix} (-1 \leq j \leq 1, -1 \leq k \leq 1)$$

or $$b[j,k] = \begin{bmatrix} 1 & 1 & 1 \\ 1 & 0 & 1 \\ 1 & 1 & 1 \end{bmatrix} (-1 \leq j \leq 1, -1 \leq k \leq 1)$$

or other kernel filters which can be used in object recognition.

Then:

$$I_{new} = I_{Intermediate} - I_{original}$$

Digital Image Resizing, Subsetting and Zooming

For an image that has a size of M, N:

$$I = I[m,n] \quad (0 \leq m \leq M-1, 0 \leq n \leq N-1, 0 \leq I \leq I_{max})$$

The image can be cropped to an image the size of J,K. This can be done in a variety of methods, e.g., nearest pixel cropping, linear interpolation, and interpolation through conversion back and forth from the digital spatial frequencies.

A first method, called nearest neighbor interpolation is processed as follows. For an image $I_{old}[m,n]$ which is resized to an image $I_{new}[j,k]$, the equation that instructs how (m,n) relate to (j,k) is:

$$j = f_1(m,n)$$

$$k = f_2(m,n)$$

Similarly, two relations exist:

$$m = g_1(j,k)$$

$$n = g_2(j,k)$$

Since (m,n) and (j,k) are integer numbers, a method of interpolation (or finding a value of a function between two specified functions) is used. One method is the nearest neighbor method. In this method:

$$m_{image} = g_1(j,k)$$

$$n_{image} = g_2(j,k)$$

Then:

$$I_{new}[j,k] = I[\text{round}(g_1(j,k)), \text{round}(g_2(j,k))]$$

i.e., for each j and k, the m is calculated and rounded to the nearest integer, the n value is calculated and rounded to the nearest integer, and the light intensity of the pixel at I(m,n) is used.

A second method, called linear interpolation, uses the function:

$$I_{new}[j,k] = x(I[m_c,n_f] - I[m_f,n_f]) + y(I[m_f,n_c] - I[m_f,n_f]) + xy(I[m_c,n_c] + I[m_f,n_f] - I[m_c,n_f] - I[m_c,n_f]) + I[m_f,n_f]$$

where $$x = m - m_f$$

$$y = n - n_f$$

and:

$$m = g_1(j,k)$$

$$n = g_2(j,k)$$

$$m_f = \text{round\_down}(m)$$

$$m_c = \text{round\_up}(m)$$

$$n_f = \text{round\_down}(n)$$

$$n_c = \text{round\_up}(n)$$

By using this function, the image can be cropped (i.e., portions at the edge of the image can be removed), the image can be translated, the image can be zoomed in or out, or a smaller subset of the image can be made.

Enhanced Visual Perception

The visual acuity of the displayed image is increased by combining a continuously changing selection of pixels into the parameters that are used to stimulate the electrode (the electrode stimulation parameters, ESPs). To explain this method, imagine that a sieve is placed over the lens of a camera video camera. The sieve will have properties corresponding to each dot (or pixel) of light that can be seen by the camera. Each hole in the sieve could correspond to one percept, consisting of ESPs of one or more electrodes. The technique described allows for patient or automatic selection of changes to:

1) the size of the holes of the sieve
2) the placement of the image with respect to the sieve In normal human vision, small movements of the eye allow for an integration of the information passed to the brain. These tiny movements of the eye can be compared to moving a sieve over the image. The brain processes this information into a contiguous picture. These tiny movements cause the picture that is presented to the retina to move slightly. In this embodiment of the present invention, this process may be replicated and mimicked by automatically providing dissimilar world pictures to the statically located electrodes placed on the retina. This replicates this movement through three possible methods:
1) random movement of the sieve
2) patterned movement of the sieve
3) movement of the sieve controlled by tracking the movement of the eye Enhancement is provided by changing the transfer between the captured image and the image that is displayed to the electrodes. This concept is derived from miniscule movements that the eye uses to potentially increase the acuity of vision through a process similar to time division multiplexing.

Jittering is one method of increasing the perceived resolution of the image by deriving the output pixels from different input pixels on each frame. This is seen using the equations that covert the source image to the stimulation pulses of the frames.

Given a pixelated image with luminosities $I(m,n)\|$ ($0 < m < M$, $0 < n < N$), a stream of stimulation pulses will be generated. The stimulation pulses will correspond to the electrodes used in the system. An assignable amplitude, pulse width, pulse shape, and frequency set of numbers A for each electrode can be produced, such that $A(e)$ is the complete list of stimulation amplitudes for a specific instance in time. These parameters are the electrode stimulation parameters (ESPs).

Figure 9:
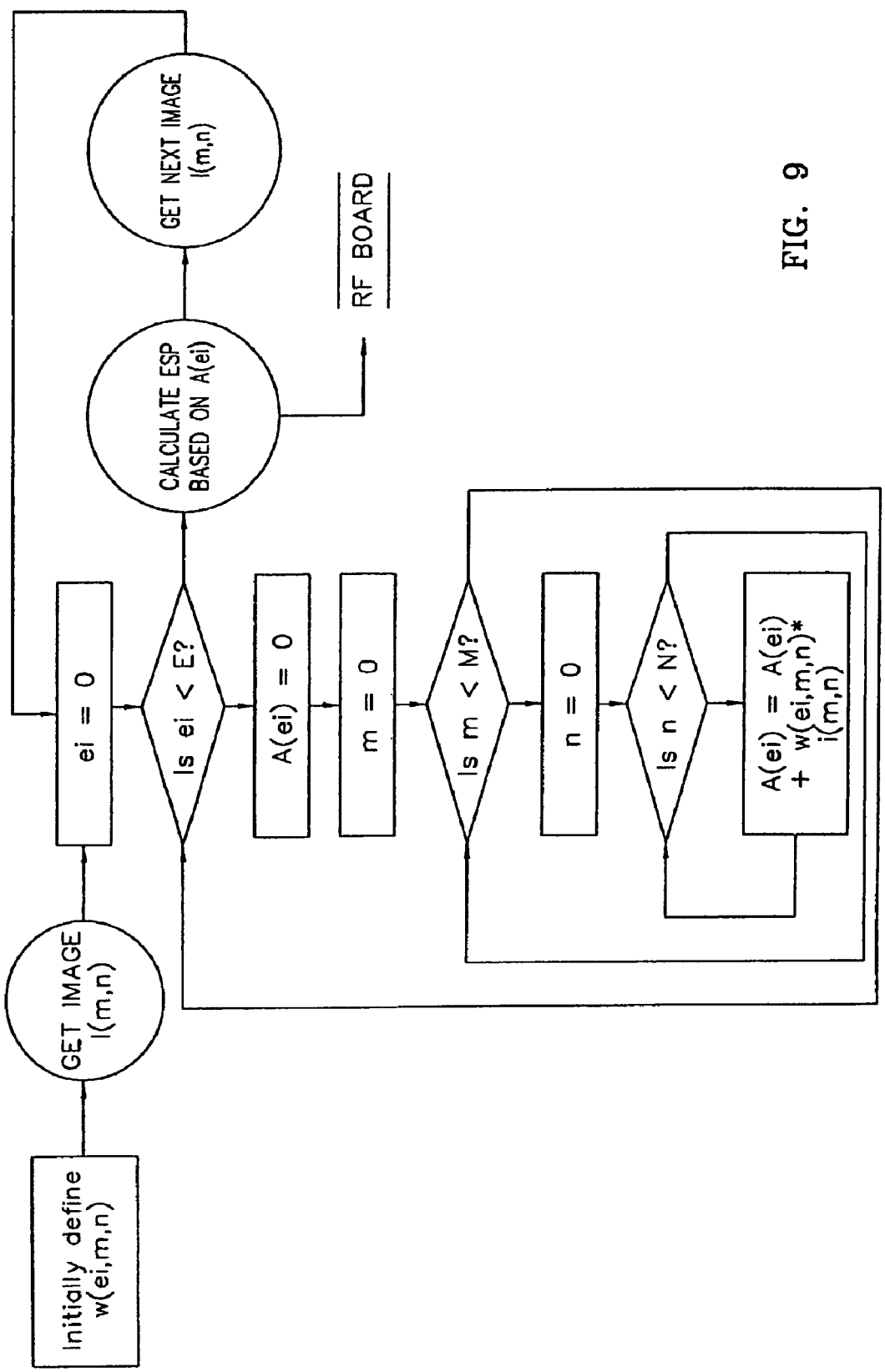
FIG. 9 is a flow chart of static mapping of image intensities to electrode stimulation parameters.

A mapping of the ESP from the pixels can be derived, and is represented in the equation:

$$A(e_i) = \sum_{n=0}^{M-1} \sum_{m=0}^{N-1} w(m, n, e_i) I(m, n)$$

where m and n are the row and column of the pixel element of the image, and M and N are the number of pixels in a row and column respectively, $w(m,n,e_i)$ is a weighting factor applied to each pixel element, and $A(e_i)$ is the ESP at electrode i. A flow chart for this technique is shown in FIG. 9.

Figure 10A:
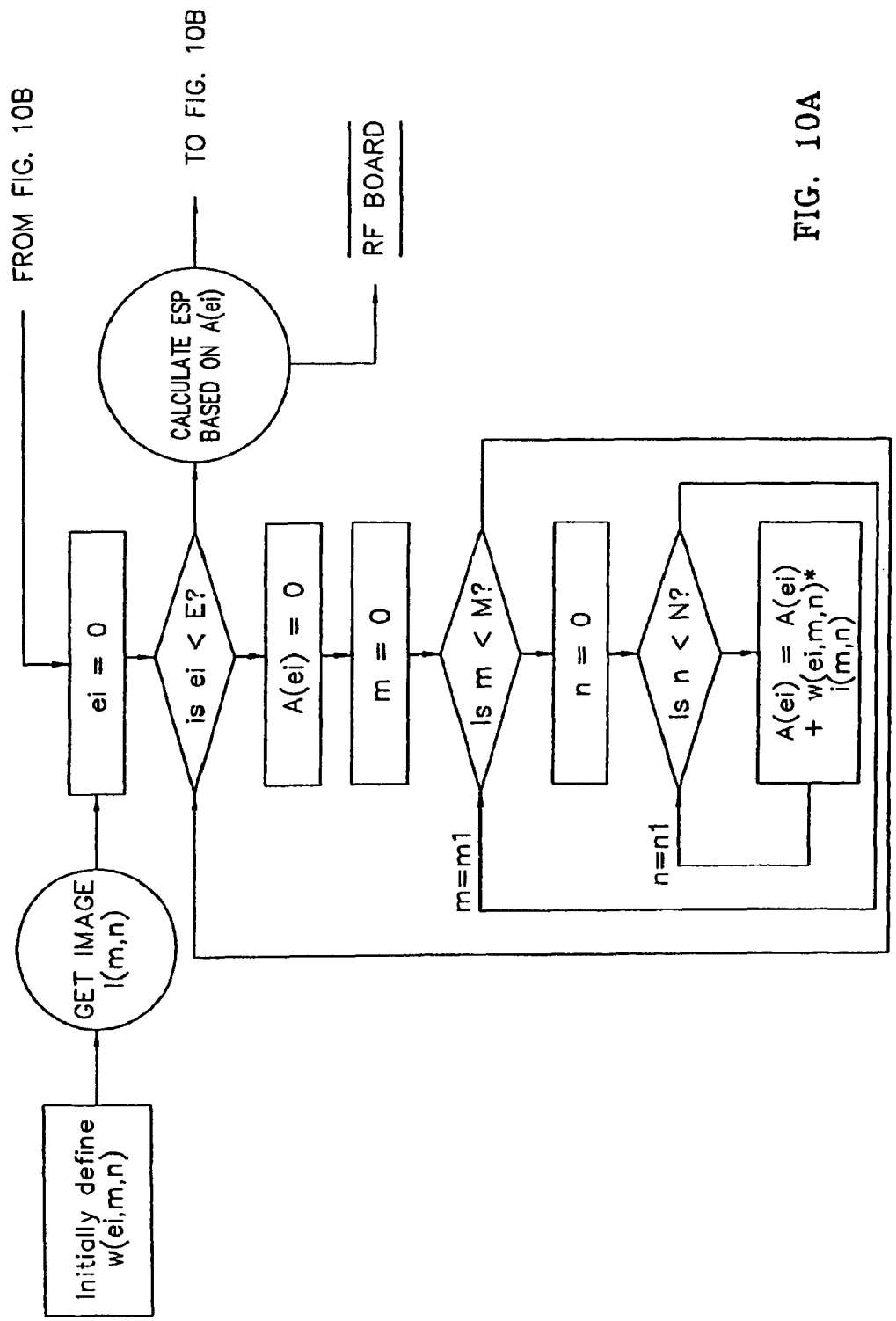
FIGS. 10A-10B comprise a flow chart of automatically controlled mapping of image intensities to electrode stimulation parameters.
Figure 10B:
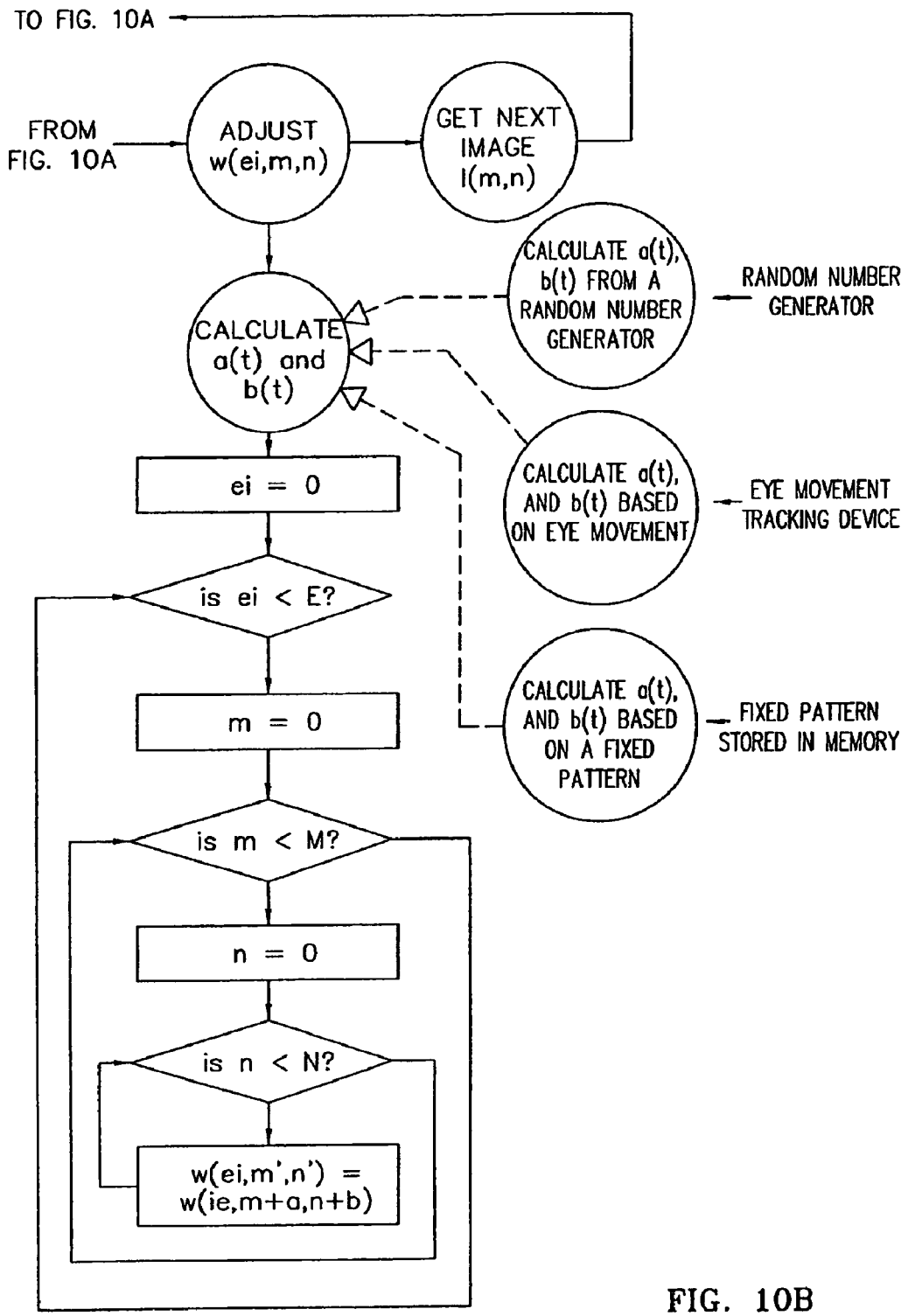

In this exemplary implementation of the present invention, changes in w correspond to scanning of the image, jittering, or slight eye movements to increase the perceived visual acuity. Essentially, the changes to the equation are changes to the weighting factor applied to each pixel in calculating the ESP. A flow chart for this procedure is seen in FIGS. 10A-10B.

For each case, the original equation is changed from:

$$A(e_i) = \sum_{n=0}^{M-1} \sum_{m=0}^{N-1} w(m, n, e_i) L(m, n)$$

to:

$$A(e_i) = \sum_{n=0}^{M-1} \sum_{m=0}^{N-1} w(m', n', e_i) I(m, n)$$

where:

$w(e_i,m',n')=w(e_i,m+\alpha(t),n+\beta(t))$

Case 1: Random Jittering a(t) and b(t) are random numbers determined from a random distribution with a definable or undefined distribution.

Case 2: Preset Scanning a(t) and b(t) have preset values that determine the rate and location of different pixel elements being summed for the ESP.

Case 3: Feedback Control of Eye Movement a(t) and b(t) are variables derived from the discrepancy between the present eye position and a defined 'neutral' or starting eye position.

Figure 11:
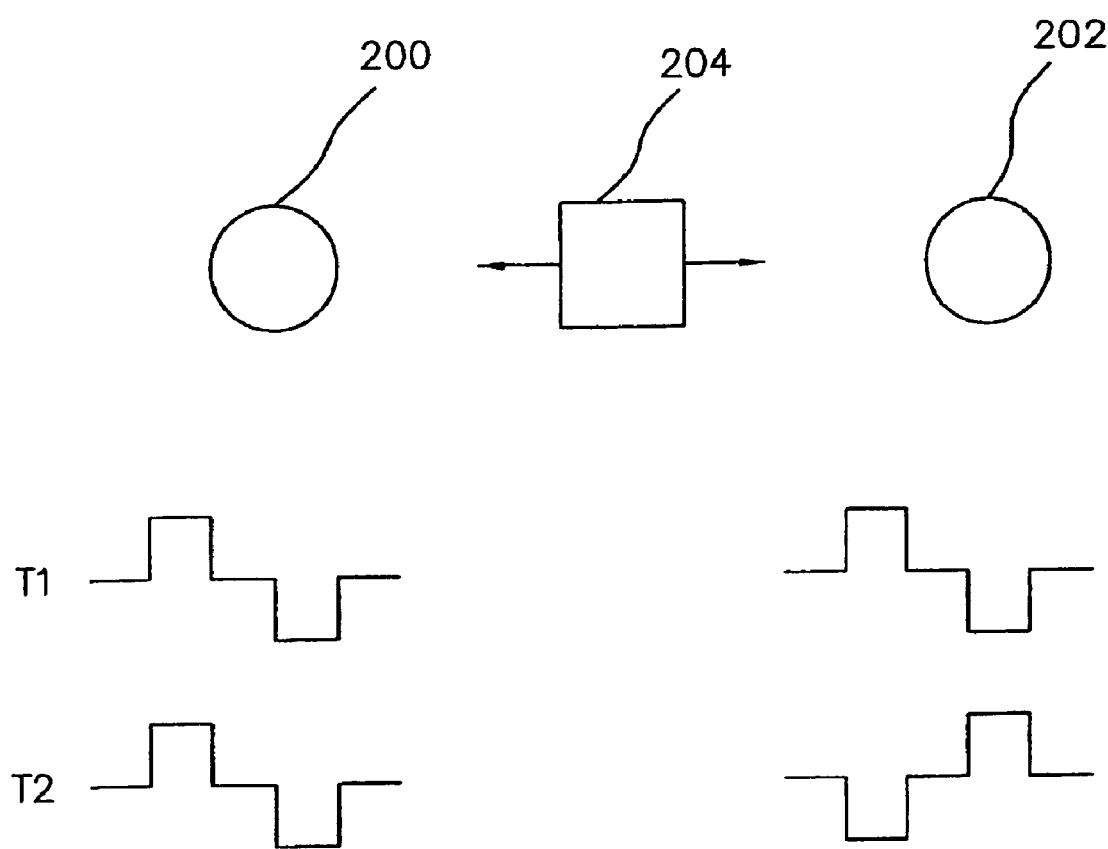

Referring now to FIG. 11, there is shown two neighboring electrodes 200 and 202 that are configured for implantation proximate to the patient's retina. In the prior art, each of the electrodes is driven independently, typically using biphasic stimulation pulses. Accordingly, each electrode results in a pixel of resolution. Thus, in this case, two electrodes result in two pixels of resolution. However, in this embodiment of the display driver 66 of the present invention, neighboring electrodes are periodically driven in combination by reversing the polarity of the signal driving one of the adjoining electrodes to generate a differential, preferably biphasic, voltage signal across the neural pathways in the retinal tissue, and thus stimulate a virtual electrode 204 (designated in this figure as ⸸). By varying the differential polarity and/or amplitude between the signal driving each of the neighboring stimulation electrodes 200, 202, the perceived position of the virtual electrode 204 can be moved to a location physically displaced from the stimulation electrodes, e.g., in-between the physical electrodes 200, 202. Alternatively, such polarity/amplitude changes may alter the stimulation level, e.g., the perceived visual brightness, of the virtual electrode 204. In an exemplary embodiment, the physical electrodes are independently driven in time period $T_1$ and in time period $T_2$, the neighboring electrodes are differentially driven to stimulate the virtual electrode 204. Accordingly, the stimulation image resolution has been increased (in this case from two to three pixels, a 50% increase). However, as will be discussed below, even more significant resolution increases may be achieved with embodiments of the present invention.

Some undesirable interactions may occur between the signals driving physical electrodes 200, 202 during $T_1$, e.g., creating another virtual electrode. Accordingly, in some embodiments of the present invention, it may be desirable to separate time period $T_1$ into two phases, $T_{1a}$ and $T_{1b}$ (not shown), where physical electrode 200 is stimulated in phase $T_{1a}$ and electrode 202 is stimulate in phase $T_{1b}$. By stimulating neighboring electrodes during different time periods, any undesirable creation of a virtual electrode may be eliminated. The use of such additional stimulation time periods for the actual electrodes may be used as needed (though not expressly discussed) in the following embodiments.

Additionally, it is not anticipated that the virtual electrodes will be as effective as the physical electrodes. Accordingly, in embodiments of the present invention, the differential signals between the physical electrodes are preferably increased in amplitude and/or duty cycle to compensate.

Figure 12:
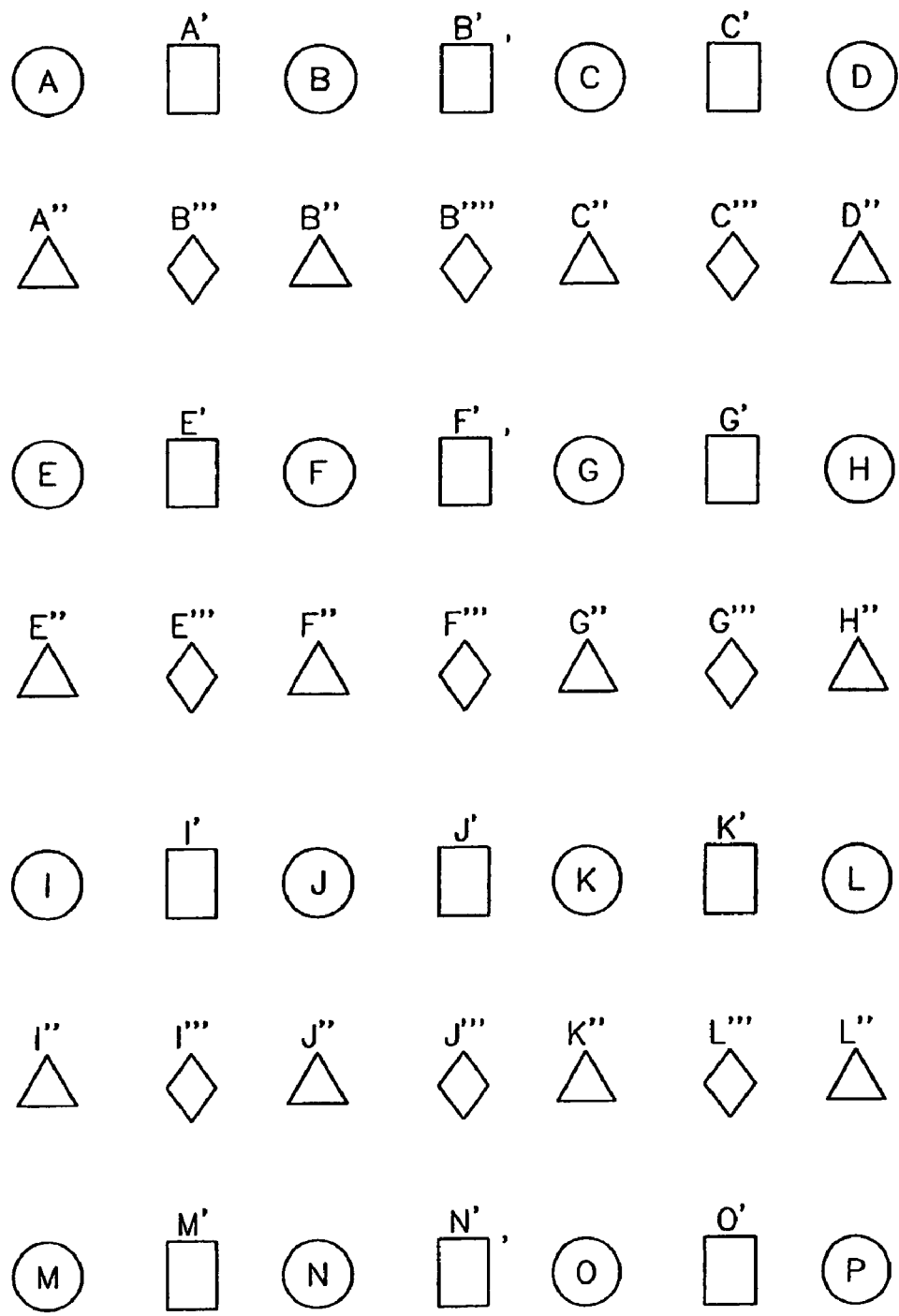

FIG. 12, shows a 4×4 array of electrodes (a more detailed example of that shown in FIG. 11). Between each of the physical electrodes designated by the symbol "O" is a virtual electrode designated by the symbol "⸸", "Δ", or "◊" as well as a single, double or triple prime, each of which corresponds to time phases for generating the virtual electrodes. An exemplary stimulation cycle pattern for FIG. 12 is shown in FIG. 13. In this exemplary pattern, the actual electrodes A-P are stimulated during phase $T_1$. During $T_2$, a first set of pairs of neighboring horizontal electrodes are stimulated, e.g., electrodes A and B (designated as A/B or A'), and a virtual electrode designated by the symbol "⊢" results. During $T_3$, a next set of pairs of neighboring horizontal electrodes are stimulated, e.g., electrodes B and C (designated as B/C or B'), and a virtual horizontal electrode designated by the symbol "⊢" results. This next (or equivalent) stimulation phase is required since some electrodes, e.g., electrode B, are required in each phase and can only provide a differential signal to one of its neighboring electrodes at a time. This process similarly continues for time periods $T_4$ and $T_5$ for generating virtual vertical electrodes "Δ" and "Δ'"

During time periods $T_6$ through $T_{12}$, virtual diagonal electrodes "◇" are generated. These virtual electrodes are preferably generated in multiple phases since some of the same physical electrodes are required to generate each of the virtual electrodes, e.g., electrodes B and E (designated as B/E or B''') generate one virtual electrode during time period $T_6$ while one of the same electrodes, e.g., electrode E (see E/J or E'''), generate another virtual electrode during time period $T_8$. Additionally, the proximity of the physical electrodes may cause undesirable virtual electrodes to be created unless a the stimulation cycle pattern is staggered. Geometrically, the diagonal physical distance between the physical electrodes is greater than the horizontal or vertical physical distances. Accordingly, the differential amplitudes and/or pulse durations associated with generating diagonal virtual electrodes are preferably greater than that used for generating horizontal virtual electrodes which, in turn is greater than the amplitude and/or pulse durations for the physical electrodes.

Figure 14:
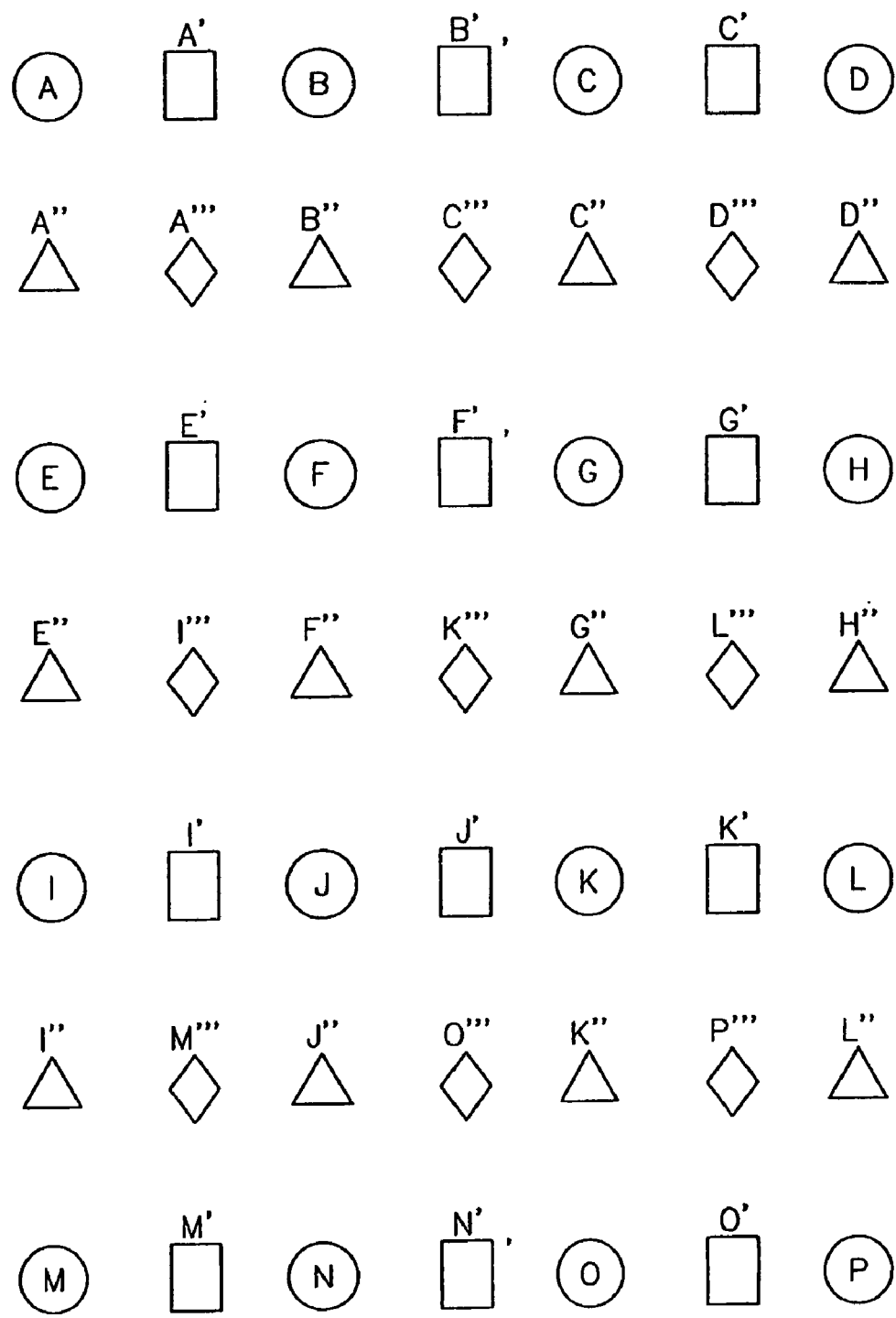

Alternatively, as seen in reference to FIGS. 14 and 15, for generating the diagonal virtual electrodes, a common electrode may be driven with a negative biphasic signal, e.g., similar to that shown in phase $T_2$ of FIG. 11 for stimulation electrode 202. Then, multiple diagonally related stimulation electrodes can be simultaneously driven with positive biphasic signals of different values for each of the corresponding virtual diagonal electrodes. For example, electrode F may be the common electrode and electrodes A, C, I, and K can be driven simultaneously during phase $T_6$ to generate the virtual diagonal electrodes, A''', C''', I''', and K''', respectively. Accordingly, in the example of FIG. 14, the virtual electrodes are driven in three less stimulation phases. Clearly, one of ordinary skill in the art may determine numerous other stimulation patterns that take advantage of the previously described techniques.

What is striking about these examples is that for 16 physical electrodes, 49 total electrodes (physical plus virtual) have resulted, i.e., slightly over a three fold increase in resolution is achieved. This technique allows a higher resolution video source to be used to stimulate a lower resolution electrode array. In the general case of an exemplary array of N×N electrodes, this technique allows for a (2*N−1)×(2*N−1) array of virtual+physical electrodes. Accordingly, the ratio of virtual+physical electrodes to physical electrodes is:

$$(4*N^2 - 4*N + 1)/(N^2)$$

which for large values of N approaches a four fold resolution increase. This level of resolution increase only requires that the virtual electrodes be able to be physically located in-between the physical electrodes, e.g., directly between. Should the perceivable position of the virtual electrodes be alterable, e.g., by altering the magnitude of the differential biphasic signals, the resolution increase may be able to be increased even further.

The aforedescribed techniques can be used in various combinations. For example, only the horizontal resolution could be increased, only the vertical resolution could be increased, both the horizontal and vertical resolutions could be increased, the use of diagonal vertical electrodes could be used (or not), etc. Any single technique or combination of these techniques, where the "high" resolution" source is at least twice the resolution of the "low" resolution physical electrode array, are considered to be within the scope of the present invention.

Additionally, the perceived resolution may be further increased by the aforedescribed use of virtual electrodes with the aforedescribed use of subsetting alterations, e.g., "jittering" to provide improved perceived visual acuity to the patient. Preferably, as described above, the selection of the employed algorithm, is alterable via inputs from the patient input device 66.

Accordingly, what has been shown is a visual, e.g., video, processing technique that is of particular use with an implantable medical device, e.g., a retinal prosthesis, for improving visual acuity. While the invention has been described by means of specific embodiments and applications thereof, it is understood that numerous modifications and variations could be made thereto by those skilled in the art without departing from the spirit and scope of the invention. For example, while the invention has been specifically described for use in processing a high resolution video signal to drive a retinal (or cortical) prosthesis, it is believed that such processing will additionally provide benefit when the low resolution output device is a video output display, e.g., LCD display, that has a lower resolution than the video input signal. Additionally, the description and the illustrated input pixel arrays and subsets have been square in shape, i.e., with symmetrical aspect ratios, that correspond to a similar square aspect ratio for the output pixel array. However, the aspect ratios of the input and output pixel arrays need not be the same. Accordingly, embodiments where the input pixel data is processed, e.g., formed into subsets by the video processor, to compensate for the difference in these aspects ratios are considered to be within the scope of the present invention. Additionally, embodiments of the present invention may use subsets that are square, rectangular, circular, oval, non-overlapping or overlapping. Furthermore, while the previous description was generally directed toward the use of transformation filters that operated on the pixel subsets, embodiments that use transformation filters to process the input video prior to subsetting are also considered to be within the scope of the present invention.

It is therefore to be understood that within the scope of the claims, the invention may be practiced otherwise than as specifically described herein.

What is claimed is:

1. An apparatus for providing vision to a visually-impaired patient, said apparatus comprising:

a high resolution optical input device for receiving an optical signal and providing a video signal in response thereto;

an eye movement sensor providing eye movement data;

a video processor for receiving said video signal as an array of pixels and said eye movement data, wherein said video processor selects subsets of said input pixels and processes said selected subsets to determine an output pixel value for each said selected subset and wherein said pixels that are selected to form said subsets are altered in response to said eye movement data and in the same direction as the eye movement to emulate the effects of saccadic eye movements;

an array of electrodes configured for implantation proximate to the retina of the visually-impaired patient, wherein said electrodes respond to electrical signals for stimulating neural pathways at the patient's retina to generate a pixelated image; said pixelated image having a resolution of no more than one fourth of the image resolution available from said high resolution optical input device; and a display driver providing electrical signals for driving said array of electrodes in response to said processed pixel values from said video processor.

2. The apparatus of claim 1 wherein said high resolution video input device is a video camera that has at least 10,000 pixels of resolution.

3. The apparatus of claim 1 wherein said high resolution video input device outputs a video signal having at least 10,000 pixels of resolution.

4. The apparatus of claim 1 additionally wherein said video processor additional comprising means for outputting a neural output signal to signal the patient's brain that the selected pixels in each subset have been altered.

5. The apparatus of claim 1 wherein said video processor additionally alters the magnitude of the subset alteration according to said eye movement data.

6. The apparatus of claim 1 wherein said video processor additionally alters the magnitude of the subset alteration according to data within at least one of said pixel subsets.

7. The apparatus of claim 1 wherein said video processor includes at least one transformation filter.

8. The apparatus of claim 7 wherein said transformation filters are selected from the set of object recognition filters, saccadic filters, image stabilization filters, histogram filers, contrast and brightness filters, edge enhancement filters, repositioning filters, image cropping filters, image zoom filters, image resizing filters, image subsetting filters, electrode stimulation filters, and motion detections filters.

9. The apparatus of claim 7 wherein at least one transformation filter in said video processor operates on said video signal.

10. The apparatus of claim 1 wherein at least one transformation filter in said video processor operates on said selected subsets of said input pixels.

11. The apparatus of claim 1 wherein said video processor varies the range of input pixel values.

12. The apparatus of claim 11 wherein said video processor varies the range of processed input pixel values to perform an automatic gain control function.

* * * * *